(12) United States Patent
Beaudet et al.

(10) Patent No.: US 8,623,282 B2
(45) Date of Patent: *Jan. 7, 2014

(54) DEVICE AND METHODS FOR QUANTIFYING ANALYTES

(75) Inventors: Matthew P. Beaudet, Eugene, OR (US); David C. Hagen, Eugene, OR (US); Jill Hendrickson, Eugene, OR (US); Rich B. Meyer, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,713

(22) Filed: Sep. 12, 2012

(65) Prior Publication Data

US 2013/0011829 A1 Jan. 10, 2013

Related U.S. Application Data

(63) Continuation of application No. 11/626,842, filed on Jan. 24, 2007.

(60) Provisional application No. 60/862,422, filed on Oct. 20, 2006, provisional application No. 60/762,008, filed on Jan. 24, 2006.

(51) Int. Cl.
*G01N 21/64* (2006.01)

(52) U.S. Cl.
USPC ............... 422/82.02; 422/82.05; 422/82.08; 422/67; 436/172

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. |
| 4,295,199 A | 10/1981 | Curry et al. |
| 4,384,042 A | 5/1983 | Miike et al. |
| 4,520,110 A | 5/1985 | Stryer et al. |
| 4,542,104 A | 9/1985 | Stryer et al. |
| 4,603,209 A | 7/1986 | Tsien et al. |
| 4,608,990 A | 9/1986 | Elings |
| 4,714,763 A | 12/1987 | Theodoropulos |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,883,867 A | 11/1989 | Lee et al. |
| 4,945,171 A | 7/1990 | Haugland et al. |

(Continued)

FOREIGN PATENT DOCUMENTS

EP 1065250 12/2004
JP 64-121 1/1989

(Continued)

OTHER PUBLICATIONS

U.S. Appl. No. 11/626,842, , "Office Action Mailed Aug. 12, 2010", 2.

(Continued)

*Primary Examiner* — Robert Xu
(74) *Attorney, Agent, or Firm* — Life Technologies Corporation

(57) ABSTRACT

The present invention relates to devices and methods for measuring the quantity of multiple analytes in a sample. The device is designed such that each of the analyte sensing elements is configured to measure the quantity of a predetermined analyte and where the machine executable instructions are configured to select the proper analyte sensing element corresponding to the analyte to be measured.

16 Claims, 7 Drawing Sheets

(56) References Cited

U.S. PATENT DOCUMENTS

| | | |
|---|---|---|
| 4,957,870 A | 9/1990 | Lee et al. |
| 4,981,977 A | 1/1991 | Southwick et al. |
| 5,055,556 A | 10/1991 | Stryer et al. |
| 5,132,432 A | 7/1992 | Haugland et al. |
| 5,187,288 A | 2/1993 | Kang et al. |
| 5,196,306 A | 3/1993 | Bobrow et al. |
| 5,208,148 A | 5/1993 | Haugland et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,314,805 A | 5/1994 | Haugland et al. |
| 5,316,906 A | 5/1994 | Haugland et al. |
| 5,362,628 A | 11/1994 | Haugland et al. |
| 5,405,975 A | 4/1995 | Kuhn et al. |
| 5,410,030 A | 4/1995 | Yue et al. |
| 5,433,896 A | 7/1995 | Kang et al. |
| 5,436,134 A | 7/1995 | Haugland et al. |
| 5,442,045 A | 8/1995 | Haugland et al. |
| 5,443,986 A | 8/1995 | Haughland et al. |
| 5,451,343 A | 9/1995 | Neckers et al. |
| 5,453,517 A | 9/1995 | Kuhn et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,516,864 A | 5/1996 | Kuhn |
| 5,534,416 A | 7/1996 | Millard et al. |
| 5,569,587 A | 10/1996 | Waggoner |
| 5,569,766 A | 10/1996 | Waggoner et al. |
| 5,576,424 A | 11/1996 | Mao et al. |
| 5,582,977 A | 12/1996 | Yue et al. |
| 5,583,001 A | 12/1996 | Bobrow et al. |
| 5,616,502 A | 4/1997 | Haugland et al. |
| 5,627,027 A | 5/1997 | Waggoner |
| 5,648,270 A | 7/1997 | Kuhn et al. |
| 5,658,751 A | 8/1997 | Yue et al. |
| 5,660,791 A | 8/1997 | Brenneman et al. |
| 5,696,157 A | 12/1997 | Wang et al. |
| 5,731,158 A | 3/1998 | Bobrow et al. |
| 5,773,236 A | 6/1998 | Diwu et al. |
| 5,798,276 A | 8/1998 | Haugland et al. |
| 5,808,044 A | 9/1998 | Brush et al. |
| 5,830,912 A | 11/1998 | Gee et al. |
| 5,846,737 A | 12/1998 | Kang |
| 5,863,753 A | 1/1999 | Haugland et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,013,802 A | 1/2000 | Hoyland et al. |
| 6,043,025 A | 3/2000 | Minden et al. |
| D423,102 S | 4/2000 | Mertenat |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,144,448 A | 11/2000 | Mitoma |
| 6,162,931 A | 12/2000 | Gee et al. |
| 6,214,560 B1 | 4/2001 | Yguerabide et al. |
| 6,316,267 B1 | 11/2001 | Bhalgat et al. |
| 6,339,392 B1 | 1/2002 | Ashihara et al. |
| 6,428,667 B1 | 8/2002 | Glazer et al. |
| 6,562,632 B1 | 5/2003 | Szalecki et al. |
| 6,586,193 B2 | 7/2003 | Yguerabide et al. |
| 6,664,047 B1 | 12/2003 | Haugland et al. |
| 6,714,299 B2 | 3/2004 | Peterson et al. |
| 6,716,979 B2 | 4/2004 | Diwu et al. |
| 6,830,731 B1 | 12/2004 | Buechler et al. |
| 6,962,992 B2 | 11/2005 | Martin et al. |
| 6,967,251 B2 | 11/2005 | Haugland et al. |
| 6,974,873 B2 | 12/2005 | Leung et al. |
| 6,977,305 B2 | 12/2005 | Leung et al. |
| D516,217 S | 2/2006 | Brown et al. |
| D522,656 S | 6/2006 | Orr et al. |
| 7,129,346 B2 | 10/2006 | Gee et al. |
| 7,138,089 B2 | 11/2006 | Aitken et al. |
| D545,705 S | 7/2007 | Voege |
| D547,216 S | 7/2007 | Rounds et al. |
| D551,578 S | 9/2007 | Kuriger et al. |
| D555,021 S | 11/2007 | Rounds et al. |
| 7,396,926 B2 | 7/2008 | Tsien et al. |
| 251,820 A1 | 11/2008 | Hendrickson et al. |
| D580,285 S | 11/2008 | Hendrickson et al. |
| 2002/0138222 A1 | 9/2002 | Carpenter et al. |
| 2003/0031595 A1 | 2/2003 | Kirchheve et al. |
| 2003/0223906 A1 | 12/2003 | McAllister et al. |
| 2004/0171034 A1 | 9/2004 | Agnew et al. |
| 2004/0253145 A1 | 12/2004 | Andersson et al. |
| 2005/0074796 A1 | 4/2005 | Yue et al. |
| 2005/0170332 A1 | 8/2005 | Shimamoto |
| 2005/0208534 A1 | 9/2005 | Dallwig et al. |
| 2005/0214810 A1 | 9/2005 | Dallwig et al. |
| 2005/0244976 A1 | 11/2005 | Gee et al. |
| 2006/0024833 A1 | 2/2006 | Gee et al. |
| 2006/0104861 A1 | 5/2006 | Windus-Smith |
| 2006/0141554 A1 | 6/2006 | Gee et al. |
| 2007/0025877 A1 | 2/2007 | Hansen |
| 2010/0255601 A1 | 10/2010 | Beaudet et al. |

FOREIGN PATENT DOCUMENTS

| | | |
|---|---|---|
| JP | 634546 | 2/1994 |
| JP | H06-034546 | 2/1994 |
| JP | 5-2168 | 2/2000 |
| JP | 52168 | 2/2000 |
| JP | 2002-350446 | 12/2002 |
| JP | 2002-350732 | 12/2002 |
| JP | 2003-207451 | 7/2003 |
| JP | 2005-214924 | 8/2005 |
| JP | 2005-536713 | 12/2005 |
| WO | WO-93/06482 | 4/1993 |
| WO | WO93/06482 | 4/1993 |
| WO | WO97/40104 | 10/1997 |
| WO | WO-97/40104 | 10/1997 |
| WO | WO99/51702 | 10/1999 |
| WO | WO-99/51702 | 10/1999 |
| WO | WO-00/67267 A | 11/2000 |
| WO | WO00/67267 A | 11/2000 |
| WO | WO-01/21624 | 3/2001 |
| WO | WO01/21624 | 3/2001 |
| WO | WO02/26891 | 4/2002 |
| WO | WO-02/26891 | 4/2002 |
| WO | 2004/017069 A1 | 2/2004 |
| WO | WO2004017069 | 2/2004 |
| WO | WO-2004017069 | 2/2004 |
| WO | WO-2007087582 A1 | 8/2007 |
| WO | WO2007087582 A1 | 8/2007 |

OTHER PUBLICATIONS

U.S. Appl. No. 11/626,842, , "Office action mailed on Mar. 25, 2011", 9 pgs.

U.S. Appl. No. 11/626,842, , "Office Action Mailed on Oct. 13, 2010".

U.S. Appl. No. 29/251,820, , "Notice of Allowance mailed Aug. 18, 2008", U.S. Appl. No. 29/251,820, NOAR, Aug. 18, 2004, 1-4.

U.S. Appl. No. 60/680,243, , "Provisional Application Expired", May 11, 2005, 1-75.

Gorevic, Peter D. et al., "Immunoglobulin G (IgG)", *Methods in Enzymology*, vol. 116, 1985, 3-25.

Haugland, Richard P., , "Molecular Probes Handbook of Fluorescent Probes and Research Products," *Ninth Edition, CD ROM, Table of Contents*, Molecular Probes, Inc., 2002, 1-6.

Haugland, Richard P. , "The Handbook; A Guide to Fluorescent Probes and Labeling Technologies", *Tenth Edition, CD-ROM*, Invitrogen / Molecular Probes Invitrogen Detection Technologies, 2005, 1-1126.

Markovits, et al., "Ethidium Dimer: A New Reagent for the Fluorimetric Determination of Nucleic Acids", *Analytical Biochemistry*, vol. 94, 1979, 259-269.

Markovits, Judith et al., "Dynamic Structure of DNA Complexes. Fluorometric Measurement of Hydrogen-Deuterium Exchange

(56) References Cited

OTHER PUBLICATIONS

Kinetics of DNA-bound Ethidium Dimer and Acridine-Ethidium Dimer", *Biochemistry*, vol. 22, No. 13, 1983, 3231-3237.

Markovits, Judith et al., "Effect of B-Z transition and nucleic add structure on the conformational dynamics of bound ethidium dimer measured by hydrogen deuterium exchange kinetics", *Nucleic Acids Research*, vol. 13, No. 10, 1985, 3773-3788.

PCT/US2007/061005 IPRP, , "International Preliminary Report on Patentability", Mailed Aug. 7, 2008, 7 pgs.

PCT/US2007/061005 ISR & WO, , "International Search Report and Written Opinion", Mailed May 25, 2007, 11 pgs.

Rye, Hays S. et al., "High-sensitivity two-color detection of double-stranded DNA with a confocal fluorescence gel scanner using ethidium homodimer and thiazole orange", *Nucleic Acids Res*, vol. 19 No. 2, 1990, 327-333.

Yguerabide, J et al., "Resonance light scattering particles as ultrasensitive labels for detection of analytes in a wide range of applications.", *J. Cell Biochem, Suppl.*, 37, 2001, 71-81.

U.S. Appl. No. 10/980,139, filed May 5, 2005, Batchelor, Robert H., et al.

U.S. Appl. No. 11/040,924, filed Oct. 13, 2005, Corry, Schuyler.

U.S. Appl. No. 11/199,641, filed Feb. 9, 2006, Patton, Wayne N.

U.S. Appl. No. 11/241,323, filed Apr. 6, 2006, Kilgore, Jason J.

U.S. Appl. No. 11/626,842, "Office Action Mailed Aug. 12, 2010", 2.

U.S. Appl. No. 11/626,842, "Office Action mailed on Mar. 25, 2011", 9 pgs.

U.S. Appl. No. 11/626,842, "Office Action Mailed on Oct. 13, 2010".

U.S. Appl. No. 29/251,820, "Notice of Allowance mailed Aug. 18, 2008", U.S. Appl. No. 29/251,820, NOAR, Aug. 18, 2008, 1-4.

U.S. Appl. No. 60/680,243, "Provisional Application Expired", May 11, 2005, 1-75.

Haugland, Richard P. "Molecular Probes Handbook of Fluorescent Probes and Research Products", *Ninth Edition, CD ROM, Table of Contents*, Molecular Probes, Inc., 2002, 1-6.

Haugland, Richard P., "The Handbook; A Guide to Fluorescent Probes and Labeling Technologies", *Tenth Edition, CD-ROM*, Invitrogen / Molecular Probes Invitrogen Detection Technologies, 2005, 1-1126.

PCT/US2007/061005 IPRP,"International Preliminary Report on Patentability", Mailed Aug. 7, 2008, 7 pgs.

PCT/US2007/061005 ISR & WO, "International Search Report and Written Opinion", Mailed May 25, 2007, 11 pgs.

Yguerabide, J et al., "Resonance light scattering particles as ultrasensitive lables for detection of analytes in wide range of applications.", *J. Cell Biochem. Suppl.*, 37, 2001, 71-81.

DEVICE AND METHODS FOR QUANTIFYING ANALYTES

CROSS-REFERENCE TO RELATED APPLICATIONS

This application claims priority as a Continuation under 35 U.S.C. §120 to U.S. patent application Ser. No. 11/626.842 filed Jan. 24, 2007 and entitled "Device and Methods for Quantifying Analytes," which in turn claims the benefit under 35 U.S.C. §119(e) to U.S. Provisional Application Ser. No. 60/862,422 filed Oct. 20, 2006 and U.S. Provisional Application Ser. No. 60/762,008 filed Jan 24, 2006. The disclosures of the above-identified applications are incorporated herein by reference as if set forth in full.

FIELD OF THE INVENTION

The present invention relates to devices and methods for measuring the quantity of an analyte in a sample using, for example, a fluorescence-based assay, an absorbance-based assay, or a light-scattering assay.

BACKGROUND OF THE INVENTION

Conventional fluorometers used to perform analyte readings, are typically designed as versatile instruments that can use several types of excitation and emission filters and may be equipped with adjustable sensitivities, so that they may be configured for many different types of assays. The Turner BioSystems TBS-380, and the BioRad VersaFluor fluorometer are examples of the typical laboratory fluorometer. A significant drawback to this design is that the user must choose the filters and/or light sources to use, requiring the user to understand how fluorescence works, look up the excitation and emission values of their assay, understand how to choose the appropriate filter sets and possibly purchase and install new filter sets. In addition, the user must often determine the appropriate gain setting (sensitivity) of the instrument by an iterative process before beginning the assay. The extensive tables that are offered with these instruments illustrate the potential difficulties for the user in setting up the instrument to perform their assay of interest. In particular, if the user intends to use only one type of assay, this selection process presents a formidable barrier to using the instrument.

In addition, conventional fluorometers typically measure light emitted from the sample and display the readout in relative fluorescence values. Because the display is in relative fluorescence values, the user must, in general, use standards to generate a standard curve, plot the relative fluorescence values of the standards, fit a line to the curve, compare the relative fluorescence value of the samples to the standard curve, and ultimately back-calculate to determine the concentration of the sample. These operations can present difficulties to the untrained user and, even for the experienced user, these operations are tedious and time-consuming. Generally, a fluorometer can be configured to download data to a computer to make this operation easier. Unfortunately, this labor-saving feature requires installation of software onto a compatible computer, which may require purchasing a compatible computer, finding an appropriate communications port to transfer the data from the instrument to the computer, finding a suitable place in the laboratory where the instrument can permanently be connected to the computer and then hoping that the installed software will operate properly with the instrument. These actions can provide formidable barriers to the would-be user.

There is at least one fluorometer, the Turner BioSystems Modulus instrument, which has some software built in for performing calculations automatically from standards provided by the user, making the performance of those select assays easier for the user. The Turner fluorometer, however, requires five standards to calculate the standard curve, requiring a significant investment of time for the user, which may be particularly tedious if the user is measuring only a small number of samples. Finally, this instrument is again designed for maximal flexibility, offering separate modules for each assay, which must be snapped into the instrument and are small enough to be easily lost in a typical laboratory environment.

Typical fluorometers also use specialized cuvettes to hold the sample. In general, the cuvettes are unique to a specific instrument, require adapters for small sample sizes, are not generally available from standard laboratory supply companies and may be expensive.

What is desired in the art is a small device for the measurement of a defined set of assays. The device should be designed for seamless integration with the specific set of assays, such that the user-interface would allow the user to choose from a defined set of assays and immediately begin to perform the assay. Upon choosing the assay of interest, the device would automatically choose the correct light sources, filter sets and sensitivity settings for the assay chosen. In addition, the device would be designed with sophisticated algorithms for data analysis appropriate for the specific assays, such that the customer need only measure a small number of standards (2 or 3). The device would also be designed to calculate a standard curve from these standards, and upon measurement of the samples, the device would automatically perform the required analysis and simply display the concentration of the sample for the user. By building automatic configurations of light sources, filter sets and gain settings and by incorporating data analysis algorithms into the device, the user would no longer encounter a learning curve just to use the device. In addition, the user would not need to choose, purchase and install filters, or determine the gain setting or sensitivity of the instrument. Finally, the user would be spared the tedium of using a large number of standards for the curve, plotting the curve, fitting a line to the curve, comparing the value of the sample to the curve, and back-calculating the concentration of the sample from the standard curve equation. The device would have a small footprint and would not require connection to a computer, such that the instrument system would not require a large dedicated amount of benchspace. In addition, because the device would not require connection to a computer for data analysis, the difficulties of finding a compatible computer for the software, installing the software on the computer and connecting the device to the computer are eliminated. Finally, the device would use a readily-available, inexpensive, disposable, laboratory test-tube to minimize the stress and expense of finding appropriate replacement cuvettes for the instrument.

SUMMARY OF THE INVENTION

The present invention relates to devices and methods for measuring the quantity of multiple analytes in a sample. In one embodiment, the device comprises a receptacle for holding a sample container having an analyte and optionally a reporter molecule, a photodetector, one or more analyte sensing elements and a computer processing unit with machine executable instructions. In turn, the analyte sensing elements comprise an energy source for exciting the sample, where the energy source is configured to emit a predetermined peak wavelength of light; an excitation filter that isolates a predetermined range of wavelengths of light from the energy source; an emission filter that isolates a predetermined range of wavelengths of light emitted from the excited sample. The device is designed such that each of the analyte sensing elements is configured to measure the quantity of a predetermined analyte and where the machine executable instructions are configured to select the proper analyte sensing element corresponding to the analyte to be measured.

The present invention also relates to devices for measuring the quantity of an analyte in a sample, with the device comprising an energy source, a photodetector, a computer processing unit with machine executable instructions and a receptacle for holding the sample tube, where the receptacle is configured to fit a microcentrifuge tube.

The present invention also relates to methods of calculating the quantity of an analyte in a sample container, with the methods comprising generating a fluorescence standard curve comprising measuring the fluorescence intensity of a low-end or blank sample (g) and measuring the fluorescence intensity of at least one high-end standard (v), wherein the curve correlates fluorescence intensity to analyte quantity, and wherein said curve has a predetermined degree of sigmoidicity (n) and curvature (k). After generation of the fluorescence standard curve, fluorescence intensity of said sample (y) is measured, where the sample comprises a fluorescent moiety capable of indicating the presence of the analyte in the sample. The fluorescence intensity of the sample (y) is then correlated to a quantity using said fluorescence standard curve.

The present invention also relates to devices for measuring the ratio of one analyte to another analyte in a sample, with the device comprising spectrally dissimilar energy sources, one or more photodetectors able to distinguish the fluorescent emission from the two analytes, a computer processing unit with machine executable instructions and a receptacle for holding the sample tube, where the receptacle is configured to fit a microcentrifuge tube.

One aspect of the present invention provides a device for measuring the quantity of multiple analytes, said device comprising
  a receptacle for holding a sample container having an analyte, a photodetector, one or more analyte sensing elements and a computer processing unit with machine executable instructions, said analyte sensing element comprising:
  a) an energy source for exciting said sample, wherein the energy source is configured to emit a predetermined peak wavelength of light;
  b) an excitation filter, wherein said the excitation filter is configured to isolate a predetermined range of wavelengths of light from the energy source;
  c) an emission filter, wherein the emission filter is configured to isolate a predetermined range of wavelengths of light emitted from the excited sample; and
  wherein each of said analyte sensing elements is configured to measure the quantity of a predetermined analyte and wherein said machine executable instructions are configured to select the proper analyte sensing element corresponding to the analyte to be measured.

In a more particular embodiment, said energy source is a light emitting diode. More particularly, said predetermined analyte is selected from the group consisting of DNA, RNA, protein, eukaryotic or prokaryotic cells, carbohydrates, lipids and metals ions. More particular still, said machine executable instructions are further configured to determine the concentration of said specific analyte based upon an emitted light from the excited sample. In another embodiment, said device further comprises a user interface. In another embodiment, said user interface comprises a display and a non-numerical keypad. In another embodiment, said sample container receptacle is configured to fit a 0.5 microcentrifuge tube. In another embodiment, said device further comprises an internal power source. Another embodiment further comprises at least one communications port. More particular still, said communications port is selected from the group consisting of a universal serial bus (USB) port, an audio/video serial bus (IEEE 1394), an infrared (IR) port and a radio frequency (RF) port.

In another embodiment, said device comprises a first and second analyte sensing elements. More particularly, said first analyte sensing element comprises a diode that emits light with a peak wavelength of about 470 nm, an excitation filter that filters out light with a wavelength of greater than about 490 nm and an emission filter that filters out light with a wavelength of less than about 520 nm and greater than about 580 nm. More particular still, said second analyte sensing element comprises a diode that emits light with a peak wavelength of about 640 nm, an excitation filter that filters out light with a wavelength of less than about 570 and greater than about 647 nm and an emission filter that filters out light with a wavelength of less than about 652 nm.

In another embodiment, the user interface is configured to allow a user to select said analyte for measurement. More particularly, the machine executable instructions are capable of selecting said analyte for measurement without user input.

In a more particular embodiment, the device is calibrated prior to the first use of said device by an end-user. Another embodiment further comprises a means for identifying an identity tag associated with said sample container. More particularly, said identity tag is machine-readable. More particular still, said identity tag is selected from the group consisting of a barcode, a data matrix barcode and a radio frequency identification (RFID) tag.

Another embodiment of the invention provides a method of detecting an analyte in a sample, said method comprising using the device described herein.

Another aspect of the invention provides a method of calculating the quantity of an analyte in a sample container, said method comprising
  a) generating a fluorescence standard curve comprising measuring the fluorescence intensity of a blank sample (g) and measuring the fluorescence intensity of at least one high-end standard (v), wherein said curve correlates fluorescence intensity to analyte quantity, and wherein said curve has a predetermined degree of sigmoidicity (n) and curvature (k);
  b) measuring the fluorescence intensity of said sample (y), wherein said sample comprises a fluorescent moiety capable of indicating the presence of said analyte in said sample; and
  c) correlating said fluorescence intensity in said sample (y) to the quantity of said analyte using said fluorescence standard curve.

In another embodiment, said analyte quantity is the concentration of said analyte. More particularly, said analyte is selected from the group consisting of DNA, RNA and protein. In another embodiment, said fluorescence standard curve approaches linearity. In a more particular embodiment, (n) is approximately 1.

In another embodiment, the curve is characterized by the equation:

$$y = r(x^n/(x^n+k)) + g; \qquad (I)$$

wherein r is a correctional value determined by the formula:

$$r=(v-g)((s^n+k)/s^n) \quad \text{(II)}$$

wherein (s) is the quantity of analyte in said high-end standard.

In another embodiment, said fluorescent moiety is a fluorescent compound selected from the group consisting of cyanine and merocyanine dyes More particularly, said the fluorescent moiety is selected from the group consisting of NanoOrange, OliGreen, PicoGreen, and RiboGreen.

In another embodiment, said high-end standard is present in said sample container. More particularly, said high-end standard is immobilized onto a solid surface.

In another embodiment, said solid surface is selected from the group consisting of the inner surface of said sample container, a bead, a chip and a fiber.

Another aspect of the invention provides a device for measuring the quantity of an analyte in a sample, said device comprising a computer processing unit with machine executable instructions that are configured to perform the method described above.

In another more particular embodiment, said device further comprises:
- a receptacle for holding a sample container having an analyte, a photodetector and one or more analyte sensing elements, said analyte sensing element comprising:
  i) an energy source for exciting said sample, wherein the energy source is configured to emit a predetermined peak wavelength of light;
  ii) an excitation filter, wherein said the excitation filter isolates a predetermined range of wavelengths of light from the energy source;
  iii) an emission filter, wherein the emission filter isolates a predetermined range of wavelengths of light emitted from the excited sample; and
  wherein each of said analyte sensing elements is configured to measure the quantity of a predetermined analyte and wherein said machine executable instructions are further configured to select the proper analyte sensing element corresponding to the analyte to be measured.

In another embodiment, said energy source is a light emitting diode. In another embodiment, said predetermined analyte is selected from the group consisting of DNA, RNA, cells, and protein.

In another said device further comprises a user interface. More particularly, said user interface comprises a display and a non-numerical keypad. In another embodiment, said user interface is configured to allow a user to select said analyte for measurement. In another embodiment, said machine executable instructions are capable of selecting said analyte for measurement without user input. In another embodiment, said device is calibrated prior to the first use of said device by an end-user. In another embodiment, said sample container receptacle is configured to fit a 0.5 ml microcentrifuge tube.

In another embodiment, said device further comprises an internal power source.

In another embodiment, said device comprises a first and second analyte sensing elements. More particularly, said first analyte sensing element comprises a diode that emits light with a peak wavelength of about 470 nm, an excitation filter that filters out light with a wavelength of greater than about 490 nm and an emission filter that filters out light with a wavelength of less than about 520 nm and greater than about 580 nm. More particular still, said second analyte sensing element comprises a diode that emits light with a peak wavelength of about 640 nm, an excitation filter that filters out light with a wavelength of less than about 570 and greater than about 647 nm and an emission filter that filters out light with a wavelength of less than about 652 nm.

Another aspect of the invention provides a device for measuring the quantity of an analyte in a sample container, said device comprising an energy source, a photodetector, a computer processing unit with machine executable instructions, and a receptacle for holding said sample container, wherein said sample container comprises a polymer selected from the group consisting of polypropylene and polyethylene.

In another embodiment, said energy source is a light emitting diode.

In another embodiment, said analyte is selected from the group consisting of DNA, RNA, protein, carbohydrates, lipids and metals ions. In another embodiment, said device further comprises a user interface. In another embodiment, said user interface comprises a display and a non-numerical keypad. More particularly, said user interface is configured to allow a user to select said analyte for measurement.

In another embodiment, said machine executable instructions are capable of selecting said analyte for measurement without user input. In another embodiment, said device further comprises an internal power source.

In another embodiment, the device further comprises at least one communications port. In another embodiment, said communications port is selected from the group consisting of a universal serial bus (USB) port, an audio/video serial bus (IEEE 1394), an infrared (IR) port and a radio frequency (RF) port. In another embodiment, said device is calibrated prior to the first use of said device by an end-user.

In another embodiment, the device further comprises a means for identifying an identity tag associated with said sample container. In another embodiment, said identity tag is machine-readable. In another embodiment, said identity tag is selected from the group consisting of a barcode, a data matrix barcode and a radio frequency identification (RFID) tag.

Another aspect of the invention provides a method of detecting an analyte in a sample, said method comprising using the device described above.

Another aspect of the invention provides a method of calculating the ratio of two analytes in a sample container, said method comprising
a) generating a fluorescence standard curve for the two analytes comprising: measuring the fluorescence intensity of a first blank analyte sample (g1) and a second analyte analyte sample (g2) and measuring the fluorescence intensity of at least one high-end standard for the first analyte (v1) and at least one high-end standard for the second analyte (v2), wherein said curve correlates fluorescence intensity to each analyte quantity or relative quantity, and wherein said curves have a predetermined degree of sigmoidicity (n) and curvature (k);
b) measuring the fluorescence intensity of said samples (y1 and y2), wherein said sample comprises a fluorescent moiety capable of indicating the presence of said analytes in said sample; and
c) correlating said fluorescence intensity in said samples (y1 and y2) to the quantity of said analyte using said fluorescence standard curve.

DETAILED DESCRIPTION OF THE INVENTION

Introduction

Figure 1:
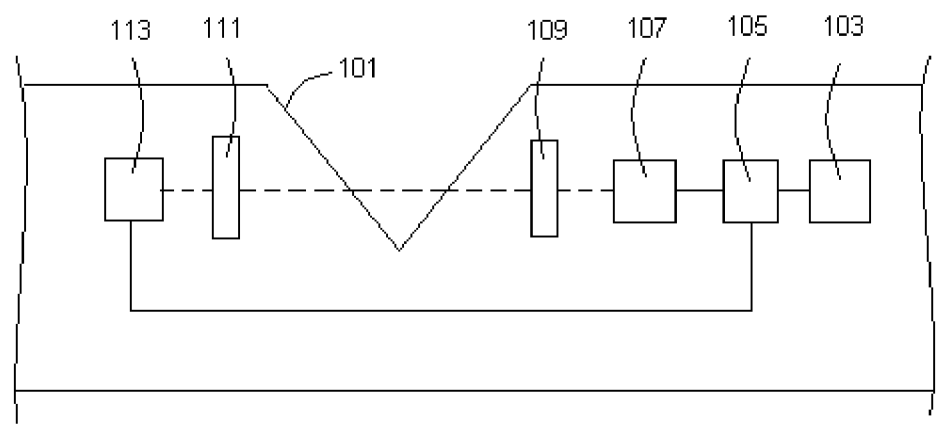
FIG. 1 depicts a side view diagram of one embodiment of the present invention.

The device and methods of present invention allow a seamless, intuitive interaction between the instrument and the user and accessibility of the methods to the user within the everyday workflow. Herein we disclose a fluorometer that comprises an analyte sensing element (ASE) that is operably linked allowing for detection of a predetermined analyte such that the selection of the predetermined analyte selects the appropriate ASE. Thus, in one embodiment the device is configured such that machine-executable instructions select the proper analyte sensing element that corresponds to the assay being used for detection of a specific analyte. The methods comprise generating a standard curve by measuring two or more standards, one of which may be a zero or blank standard. The standard curve can be generated by applying the values of the standard to a specific algorithm to generate an equation expressing the relationship between the signal generated by the assay as read by the instrument and the concentration of analyte in the sample. The device may be designed such that the user interface prompts the user to choose the assay, insert the standards, and insert the samples. From this simple input, the device automatically can choose the appropriate analyte-sensing elements and algorithm, perform the necessary calculations to determine the standard curve, and compare the signal from the sample to the standard curve and perform the necessary calculations to show the quantity of the analyte in the sample as a readout for the user. In addition, the device may also be configured to accept an inexpensive, disposable plastic, optically clear microcentrifuge-shaped tube that holds the standards or samples and are readily available. Furthermore, the device can be used to monitor and quantify multiple analytes in the same sample by, for example, labeling analytes with different dyes and then exciting and/or filtering emission spectra at particular wavelengths such that the dye/analyte of interest can be distinctly monitored in the presence of other dyes/analytes.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a reporter molecule" includes a plurality of reporter molecules and reference to "a fluorometer" includes a plurality of fluorometers and the like.

Unless defined otherwise, all technical and scientific terms used herein have the same meaning as commonly understood by one of ordinary skill in the art to which this invention is related. The following terms are defined for purposes of the invention as described herein.

The term "analyte" refers to a molecule that is to be measured or detected in the assay of this invention. The term "analyte" includes any substance for which there exists a specific binding molecule, or for which a specific binding molecule can be prepared, or for which the analyte interacts with a reporter molecule to create a detectable signal. Representative analytes include, but are not limited to, drugs, antigens, haptens, antibodies, proteins, peptides, amino acids, hormones, steroids, cancer cell markers, tissue cells, viruses, vitamins, nucleic acids, metal ions, enzymes, lipids, radioactive isotopes, viruses, bacteria, pathogens, chemical contaminants, and pesticides.

The term "analyte sensing elements" or "ASE" as used herein refers to a particular combination of 1) an energy source which itself may emit a restricted range of wavelengths of electromagnetic energy, 2) an "excitation filter" which is capable of isolating a range of wavelength of electromagnetic energy, such as but not limited to light, and 3) an "emission filter" that is capable of isolating a range of wavelength of electromagnetic energy that is emitted from the sample wherein the three parts are operably linked. The ASE are operably linked such that a predetermined analyte can be measured without the manual selection of wavelength and filters or the need to perform additional calculations by the end user.

The term "aqueous solution" as used herein refers to a solution that is predominantly water and retains the solution characteristics of water. Where the aqueous solution contains solvents in addition to water, water is typically the predominant solvent.

The term "buffer" as used herein refers to a system that acts to minimize the change in acidity or basicity of the solution against addition or depletion of chemical substances.

The term "detectable response" as used herein refers to an occurrence of, or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of these parameters. Alternatively, the detectable response is an occurrence of a signal wherein the dye is inherently fluorescent and does not produce a change in signal upon binding to a metal ion or phosphorylated target molecule. Alternatively, the detectable response is the result of a signal, such as color, fluorescence, radioactivity or another physical property of the detectable label becoming spatially localized in a subset of a sample such as in a gel, on a blot, or an array, in a well of a microplate, in a microfluidic chamber, or on a microparticle as the result of formation of a ternary complex of the invention that comprises a phosphorylated target molecule.

The term "energy source" as used herein refers to a light or wavelength emitting device, preferably an LED, capable of exciting particles in solution.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as semiconductor nanocrystals and other fluorophores described in RICHARD P. HAUGLAND, MOLECULAR PROBES HANDBOOK OF FLUORESCENT PROBES AND RESEARCH CHEMICALS (10$^{th}$ edition, 2005).

The term "kit" as used herein refers to a packaged set of related components, typically one or more compounds or compositions.

The term "label" as used herein refers to a chemical moiety or protein that retains it's native properties (e.g. spectral properties, conformation and activity) when attached to a labeling reagent and used in the present methods. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9$^{th}$ edition, CD-ROM, September 2002), supra.

The term "machine executable instructions" as used herein refers to a set of instructions that cause a machine, such as a CPU, to perform a method or assay.

The term "photodetector" as used herein refers to any device that is capable of accepting an optical signal and producing an electrical signal containing the same information as in the optical signal.

The term "predetermined analyte" as used herein refers to an analyte that is coordinated with an analyte sensing element (ASE) such that selection of the predetermined analyte dictates the particular ASE present in the device.

The terms "protein" and "polypeptide" are used herein in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

The term "sample" as used herein refers to any material that may contain an analyte for detection or quantification. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or semi-solid substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides, environmental material, food stuff, industrial material and buffer solutions. The sample may be in an aqueous solution, a viable cell culture or immobilized on a solid or semi solid surface such as a glass or plastic tube or cuvette.

Fluorometer and Methods of Use

One aspect of the present invention provides a device comprising a receptacle for holding a sample container having an analyte and optionally a reporter molecule, a photodetector, one or more analyte sensing elements and a computer processing unit with machine executable instructions. In turn, the analyte sensing elements comprise an energy source for exciting the sample, where the energy source is configured to emit a predetermined peak wavelength of light; an excitation filter that isolates a predetermined range of wavelengths of light from the energy source; an emission filter that isolates a predetermined range of wavelengths of light emitted from the excited sample. The device is designed such that each of the analyte sensing elements is configured to measure the quantity of a predetermined analyte and where the machine executable instructions are configured to select the proper analyte sensing element corresponding to the analyte to be measured.

FIG. 1 is a side view diagram of one embodiment of the present invention. FIG. 1 represents one embodiment of the architecture of the elements of the devices and it will become apparent to one of skill in the art as to how to implement alternative architectures to achieve the functionality of the devices of the present invention. The system illustrated in FIG. 1 comprises a receptacle for holding a sample container 101, a power source 103, a computer processing unit 105, an analyte sensing element which comprises an energy source 107, an excitation filter 109 and an emission filter 111, and a photodetector 113.

In one embodiment, the device is not limited by the sample container for which the receptacle is configured to receive. Example of sample containers that the receptacle may fit include but are not limited to, petri dishes, culture flasks, 4-well plates, 8-well plates, 24-well plates, 96-well plates, cuvettes, centrifuge tubes, and microcentrifuge tubes to name a few. As used herein a "receptacle being configured to fit or receive" means that the receptacle for the sample container is designed such that the sample container fits snuggly into the opening, allowing little or no movement of the sample container, beyond the vertical axis. In addition, the receptacle and the computer processing unit may or may not be coordinated to one another such that, unless the sample container is positioned properly in the receptacle, the computer processing unit will not initiate a measurement of the sample. The receptacle may accept only 1 sample container, or it may be configured to accept 2, 3, 4, 5, 6, 7, 8, 9 10 or more sample tubes. In one embodiment, the receptacle is configured to fit or receive a microcentrifuge tube. Examples of microcentrifuge tubes are well know in the art and include but are not limited to Eppendorf™ tubes, optically—clear microcentrifuge-shaped tubes such as those used in real-time PCR experiments (an example is the Axygen PCR-05-C 500 µL PCR tube available from VWR) and generic centrifuge tubes. In a more particular embodiment, the receptacle may be configured to fit only one size microcentrifuge tube or it may be configured to fit more than one size of microcentrifuge tubes including, but not limited to, less than 0.5 ml tubes, 0.5 ml tubes, 1.5 ml tubes, 2 ml tubes and greater than 2 ml tubes.

Accordingly, in one embodiment, the present invention relates to a device for measuring the quantity of an analyte in a sample container, where the device comprises an energy source, a photodetector, a computer processing unit with machine executable instructions and a receptacle for holding the sample container, where the sample container comprises an optically clear plastic. In one specific embodiment, the plastic is comprised of polypropylene and/or polyethylene. Real-time PCR instruments, such as the BioRad DNA Engine and the Opticon 2 Real-Time PCR Detection System are examples of instruments that use this type of tube for a sample requiring a fluorophore for detection. This type of instrument and the corresponding tubes are in common use, and thus the tubes are readily available from many sources.

The device of the present invention also comprises a photodetector. The photodetector can be any device that is capable of accepting an optical signal and producing an electrical signal containing the same information as in the optical signal. Examples of photodetectors that may be used in the present invention include, but are not limited to, photoresistors, photovoltaic cells, photodiodes, photomultipliers, phototubes, phototransistors and pyroelectric devices that detect changes in temperature due to illumination.

The device of the present invention also comprises one or more analyte sensing elements. Each of the analyte sensing elements of the present invention comprise a particular combination of 1) an energy source which itself may emit a restricted range of wavelengths of electromagnetic energy, 2) an "excitation filter" which is capable of isolating a range of wavelength of electromagnetic energy, such as but not limited to light, and 3) an "emission filter" that is capable of isolating a range of wavelength of electromagnetic energy that is emitted from the sample. Upon excitation by energy from the energy source, the sample will, generally speaking, emit a form of electromagnetic energy, such as, but not limited to light that can be generated by fluorescence, phosphorescence or luminescence. In one embodiment of the present invention, the device comprises a single analyte sensing element (ASE). In another embodiment, the device comprises more than ASE. In a more particular embodiment, the device comprises two, three, four, five, six, seven, eight, nine or ten or more ASEs. If the device comprises more than one ASE, then the multiple ASEs may share one or more individual components of the ASEs. Thus, for example, when a device of the present invention comprises two ASEs, these ASEs may share an energy source and have separate emission filters and excitation filters. To continue the example, the ASEs may share an energy source and an emission filter and have separate excitation filters. Of course, in one embodiment, the device of the present invention may comprise more than one distinct ASE, where the distinct ASEs share neither an energy source nor an emission filter nor an excitation filter. In a more particular embodiment, the device comprises more than one ASE where none of components of the ASEs are shared, although they may be integrated into or connected to the same computer processing unit.

As used herein, an energy source is a source of electromagnetic energy and includes any type of energy along the electromagnetic spectrum including, but not limited to, radio energy, microwave energy, infrared, visible light, ultraviolet light, x-ray light and even gamma radiation. In one embodiment, the energy emitted from the energy source is visible light. In a more particular embodiment, a peak wavelength of visible light is emitted from the energy source. For example, the peak wavelength of visible light may be, but is not limited to, between 400 nm and 450 nm, or between 425 and 475 nm, or between 450 nm and 500 nm, or between 475 nm and 525 nm, or between 500 nm and 550 nm, or between 525 and 575 nm, or between 550 nm and 600 nm, or between 575 nm and 625 nm, or between 600 nm and 650 nm, or between 625 and 675 nm, or between 650 nm and 700 nm, or between 675 nm and 725 nm. These peak wavelengths ideally correspond to the optimal excitation wavelength of the report molecule of choice for detection of a predetermined analyte. In another embodiment the peak wavelengths correspond to the optimal wavelength to product autofluorescence from the predetermined analyte. In yet another embodiment the peak wavelength correspond to the optimal wavelength for measuring light scatter from the predetermined analyte.

The energy source can be any device or composition that is capable of emitting electromagnetic energy. Examples of energy sources include, but are not limited to light emitting diodes (LED), incandescent light bulbs, gas discharge lamps (e.g., helium, krypton, neon, argon, sodium vapor and nitrogen), a laser, a maser, free charged particles such as ions, accelerated particles, chemiluminescent chemicals, fluorescent substances, and phosphorescent substances. In one particular embodiment, the energy source is at least one light emitting diode. In another particular embodiment, the energy source is more than one light emitting diode. In a more particular embodiment, the energy source is a single light emitting diode that emits visible light. In an even more particular embodiment, the energy source is one or more light emitting diodes that emits visible light with a predetermined peak wavelength.

Another component of the ASE of the present invention includes at least one emission filter and one excitation filter. As used herein, an excitation filter is a filter that is placed in between the energy source and the sample such that the energy emitted from the energy source is filtered prior to striking the sample. As used herein, the emission filter is a filter that is placed in between the sample and the photodetector such that the energy emitted from the sample is filtered prior to striking the photodetector. In general, filters act to exclude (filter out) certain wavelengths of electromagnetic energy from passing through the filter. Filters may exclude wavelengths of electromagnetic energy below or above a specific wavelength. For example, a filter can exclude all wavelengths of light below 650 nm or all wavelengths above 490 nm. Filters may also exclude electromagnetic energy within a specific range of wavelengths. For example, a filter may exclude all wavelengths of light except for light with a wavelength in between about 520 nm and about 580 nm. The selection of an appropriate filter for use with the energy source should be readily apparent. In one specific embodiment, the ASE comprises an energy source that emits light, an excitation filter that filters out light of wavelengths greater than about 490 nm and an emission filter than filters out light of wavelengths less than about 520 nm and greater than about 580 nm. In another specific embodiment, the ASE comprises an energy source that emits light, an excitation filter that filters out light of wavelengths less than 570 nm and greater than about 647 nm and an emission filter than filters out light of wavelengths of less than about 565 nm. In yet another embodiment, the device comprises at least two ASEs where the first ASE comprises an energy source that emits light, an excitation filter that filters out light of wavelengths greater than about 490 nm and an emission filter than filters out light of wavelengths less than about 520 nm and greater than about 580 nm, and where the second ASE comprises an energy source that emits light, an excitation filter that filters out light of wavelengths less than 570 nm and greater than about 647 nm and an emission filter than filters out light of wavelengths of less than about 565 nm.

Figure 2:
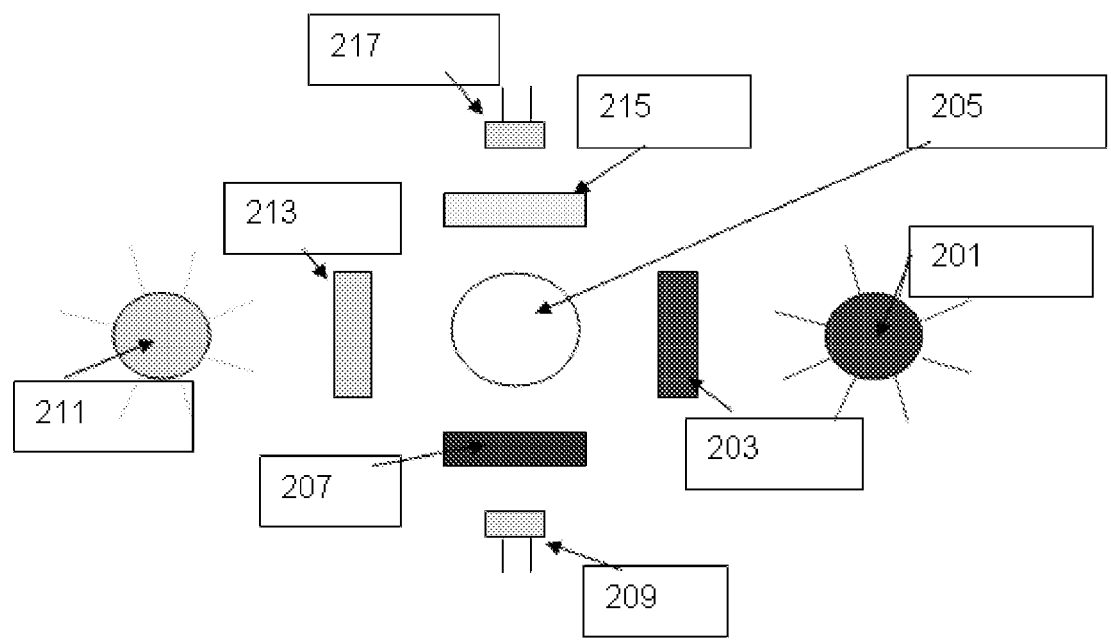
FIG. 2 depicts one embodiment of multiple analyte sensing units centered on the sample container receptacle.
Figure 3:
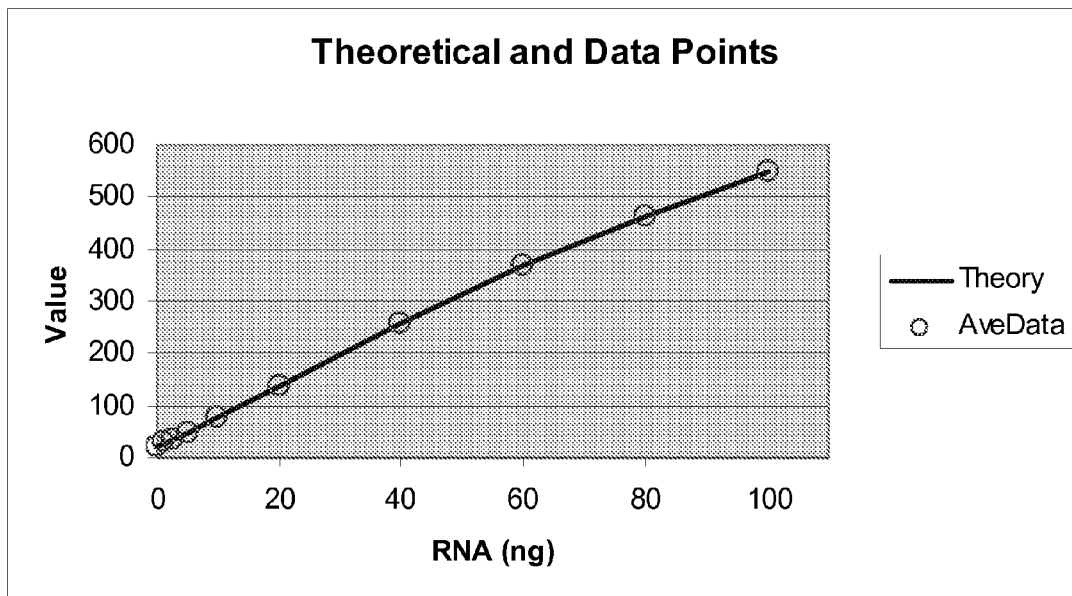
FIG. 3 depicts a theoretical fluorescence standard curve for RNA as the analyte that can be generated using equation I. The high-end standard used to generate the curve contains 100 ng of RNA, the assay reliably goes up to 200 ng when this 100 ng standard is used.

In one embodiment, the device comprises more than one ASE, and the multiple ASEs are configured in a spatial arrangement such that the core components of the ASEs do not move. FIG. 2 depicts an example of a device with 2 ASEs, where the core components of the ASEs are centered on the sample receptacle. Referring to FIG. 2, the first ASE is comprised of components 201, 203 and 207 and the second ASE is comprised of components 213, 215 and 217. In one example of this spatial configuration, energy (e.g., light) is emitted from energy source 201 (e.g., light emitting diode) and passes through excitation filter 203 before passing through the sample that is sitting in receptacle 205. Once the light strikes the sample, the light emitted from the excited sample passes through emission filter 207 and is reflected by mirror 209 into or onto a photodetector 211. Continuing this example, energy (e.g., light) is emitted from energy source 213 (e.g., light emitting diode) and passes through excitation filter 215 before passing through the sample that is sitting in receptacle 205. Once the light strikes the sample, the light emitted from the excited sample passes through emission filter 217 and is reflected by mirror 219 into or onto a photodetector 211. As is apparent from FIG. 2, mirrors may or may not be necessary to direct the energy beam into or onto the photodetector, depending on the spatial relationship between the energy emitted from the excited sample and the photodetector. Thus, one or more mirrors are optional and may be present in some specific embodiments.

The devices of the present invention also comprise a computer processing unit. The processor controls the operation of the device and also provides control of various functionalities of the device. The processor can be a central processor that controls functionality via a bus structure or other communications interface. The processor can also be implemented by distributing the processing functions among one or more of the various components utilized to implement the functionalities of the devices.

One component of the computer processing unit will include memory. Memory is used to provide storage for program data or other data used by computer processing unit during operation and can be implemented using various RAM or ROM memory devices. Memory can be used for example, to store operating instructions and to provide memory registers for operating and storage.

Memory can also be used in conjunction with a storage device such as, but not limited to, a disk storage device or a flash memory device. A storage device can also be used to store program instructions, control and calibration curves, operational data, history logs, and other data which may be desired to be stored within the device. Alternatively, the storage device, if one is present, need not be within the device. In one embodiment, the storage device will not store large amounts of data, but the data or instructions it stores is capable of being accessed frequently and rapidly. In another embodiment, a cache is present to minimize latencies associated with retrieving frequently used data or instructions from the storage device. In more specific embodiments, the storage device may store less 1 gigabyte (GB), less than 500 megabytes (MB), less than 250 MB, less than 100 MB, less than 50 MB, less than 20 MB, less than 10 MB, less than 9 MB, less than 8 MB, less than 7 MB, less than 6 MB, less than 5 MB, less than 4 MB, less than 3 MB, less than 2 MB or less than 1 MB of data and/or instructions. In another specific embodiment, the storage device may store large amounts of data, for example 1 GB or more of data.

The memory of the device will comprise machine executable instructions. The machine executable instructions control the operation of the ASEs within the device. For example, the machine executable instructions are configured to select an appropriate ASE, depending on the particular analyte being measured. Thus, in one particular embodiment the device comprises more than one ASE and comprises machine executable instructions. The end-user can select and input into the device the specific analyte to be measured and, in turn, the machine executable instructions will select and utilize the proper ASE within the device to measure the selected analyte. In a particular embodiment, the ASE has been optimized for use with a specific reporter molecule, which is used to measure the selected analyte.

For example, referring to FIG. 2, the end-user may select a specific analyte to be measured by the device and the machine executable instructions will determine which ASE to utilize. If one particular analyte is chosen, the machine executable instructions will operate to turn on power to energy source 201 and photodetector 209, but not energy source 211 or photodetector 217. Energy from energy source 201 will pass through excitation filter 203 and strike the sample sitting in receptacle 205. Energy emitted from the sample will then pass through emission filter 207 before traveling to photodetector 209. If the end-user then chooses a different analyte to measure, the machine executable instructions will operate to turn on power to energy source 211 and photodetector 217, but not energy source 201 or photodetector 209. Energy from energy source 211 will pass through excitation filter 213 and strike the sample sitting in receptacle 205. Energy emitted from the sample will then pass through emission filter 215 before traveling to photodetector in 217. In this sense, the machine executable instructions are capable of being configured to select the proper ASE that corresponds to the analyte being measured.

In another embodiment, the machine executable instructions are configured such that they are capable of selecting the analyte to be measured, without end-user input. In this embodiment, the end-used will simply place the sample container in receptacle 205. Once in place, the machine executable instructions may or may not perform one or a series of operations to determine the most appropriate ASE to use to analyze the sample. Once the machine executable instructions select the proper ASE that corresponds to the analyte within the sample, the machine executable instructions then performs the assay to determine analyte concentration.

In yet another embodiment, the machine executable instructions may also comprise calibration data, such as but not limited to, calibration curve data, internal standard data and the like. For example, the calibration data may be written into the machine executable instructions such that there is not a need for the end-user to acquire blank and standard measurement data. The machine executable instructions may thus allow the device to be calibrated prior to the first use of an end-user. And the machine executable instructions may also allow the device to be entirely "calibration free" in relation to the end-user.

In another embodiment the device monitors and quantifies multiple analytes in the same sample by, for example, labeling analytes with different dyes and then exciting and/or filtering emission spectra at particular wavelengths such that the dye/analyte of interest can be distinctly monitored in the presence of other dyes/analytes. Accordingly, a particular embodiment of the present invention provides for simultaneous monitoring of multiple analytes, such as by concomitant detection of multiple dyes/analytes in a single sample.

The devices of the present invention are designed to measure the quantity of multiple analytes in a sample. The devices may be designed to measure the multiple analytes simultaneously, or the devices may be configured to measure the analytes "one at a time." The analytes to be quantified may be any analyte, provided the device is configured to measure the specific analyte desired. As used herein, an analyte is a chemical, composition or an organism in a sample that is to be analyzed. Examples of analytes to be quantified include, but are not limited to nucleic acids such as DNA and RNA, proteins, carbohydrates, lipids, proteoglycans, glycoproteins, proteolipids, lipoproteins, metal ions, prokaryotic and eukaryotic cells, and viral particles. In one specific embodiment, the device is capable of quantifying DNA, RNA, eukaryotic and prokaryotic cells, and protein.

In one embodiment the selected analyte is measured using a reporter molecule. The term "reporter molecule" as used herein refers to any luminescent molecule that is capable of producing a visible signal when associated with an anlayte, either directly or indirectly. Included are reporter typically used in a fluorometer for detection of an analyte such as nucleic acid and proteins. Reporter molecules that are presently commercially available include, but are not limited to, the dyes in Quant-it® kits (Invitrogen), Sypro® dyes, Picogreen® dye, Deep Purple protein stain, Syto® Dyes, Sybr® dyes, Flamingo® dyes, and Lucy® dyes. Typically, luminescent molecules, as used herein include dyes, fluorescent proteins, phosphorescent dyes, chromophores, enzyme substrates, haptens and chemiluminescent compounds particles, haptens, enzymes and their colorimetric, fluorogenic and chemiluminescent substrates that are capable of producing a detectable signal upon appropriate activation. The term "dye" refers to a compound that emits light to produce an observable detectable signal. "Dye" includes fluorescent and non-fluorescent compounds that include without limitations pigments, fluorophores, chemiluminescent compounds, luminescent compounds and chromophores. The term "chromophore" as used herein refers to a label that emits and/or reflects light in the visible spectra that can be observed without the aid of instrumentation. The term "fluorophore" as used herein refers to a composition that is inherently fluorescent or demonstrates a change in fluorescence upon binding to a biological compound, i.e. can be fluorogenic or the intensity can be diminished by quenching. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, The Handbook, A Guide to Fluorescent Probes and Labeling Technologies ($10^{th}$ edition, 2005).

Numerous fluorogenic and colorimetric enzyme substrates exist for the amplification of a signal as well as substrates used to directly detect the function of an anlyte, e.g. enzymes that cleave the substrate resulting in a detectable signal. Both are included in the present invention for the detection of a predetermined analyte. In the case of the enzyme substrate used to amplify the signal the analyte is associated with an enzyme. In the case where the enzyme substrate directly detects the ananlyte, the analyte is the enzyme. Colorimetric or fluorogenic substrate and enzyme combination included, but are not limited to, uses of oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azinobis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red and Amplex Ultra Red reagent and its variants (U.S. Pat. No. 4,384,042 and U.S. Ser. No. 10/980, 139) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

In another embodiment, enzyme substrates used to detect the presence of enzymes associated with microbrial resistance to antibiotics, such as β-lactam, include beta-lactamase substrates, including, but not limited to, any substrates and method of use disclosed in U.S. Ser. No. 11/040,924; and US20030003526.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In addition to enzymes, haptens such as biotin are also preferred labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In a separate embodiment the reporter molecule is a dye or label that is conjugated to a specific binding partner, wherein the specific binding partner binds to the analyte or a molecule covalently attached to the analyte. The term "label" as used herein refers to a chemical moiety or protein that retains it's native properties (e.g. spectral properties, conformation and activity) when attached to a labeling reagent and used in the present methods. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($9^{th}$ edition, CD-ROM, September 2002), supra.

Typically the label would be an antibody, antigen, biotin or streptavidin, all conjugates typically used in an immunoassay. However, there is no intended limitation of the specific binding partner that can be conjugated to a label and used in the present methods to detect a target analyte.

TABLE 2

Representative Specific Binding Pairs

| antigen | antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| Fc region | Anti-Fc antibody |
| hormone | hormone receptor |
| ion | chelator |

In a particular aspect the carrier molecule is an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. In one aspect the carrier molecule is a Fab fragment specific to the Fc portion of the target-binding antibody or to an isotype of the Fc portion of the target-binding antibody (U.S. Ser. No. 10/118,204). The monovalent Fab fragments are typically produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$.

Alternatively, a non-antibody protein or peptide such as protein G, or other suitable proteins, can be used alone or coupled with albumin. Preferred albumins include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are conjugated to a reactive label in the same manner as the other carrier molecules of the invention.

In another aspect the carrier molecule is a whole intact antibody. Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds).

When IgG is treated with the enzyme papain a monovalent antigen-binding fragment can be isolated, referred herein to as a Fab fragment. When IgG is treated with pepsin (another proteolytic enzyme), a larger fragment is produced, F(ab')$_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define the Fab', F(ab')$_2$ and Fab portions of the antibody. It is well known in the art to treat antibody molecules with pepsin and papain in order to produce antibody fragments (Gorevic et al., Methods of Enzyol., 116:3 (1985)).

The monovalent Fab fragments of the present invention are produced from either murine monoclonal antibodies or polyclonal antibodies generated in a variety of animals that have been immunized with a foreign antibody or fragment thereof, U.S. Pat. No. 4,196,265 discloses a method of producing monoclonal antibodies. Typically, secondary antibodies are derived from a polyclonal antibody that has been produced in a rabbit or goat but any animal known to one skilled in the art to produce polyclonal antibodies can be used to generate anti-species antibodies. The term "primary antibody" describes an antibody that binds directly to the antigen as opposed to a "secondary antibody" that binds to a region of the primary antibody. Monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art.

In one aspect the antibodies are generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments.

The labels of the present invention include any directly or indirectly detectable label known by one skilled in the art that can be covalently attached to a specific binding partner. Labels include, without limitation, a chromophore, a fluorophore, a fluorescent protein, a phosphorescent dye, a tandem dye, a particle, a hapten, an enzyme and a radioisotope. Preferred labels include fluorophores, fluorescent proteins, haptens, and enzymes.

A fluorophore of the present invention is any chemical moiety that exhibits an absorption maximum beyond 280 nm, and when covalently attached to a labeling reagent retains its spectral properties. Fluorophores of the present invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486, 616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774, 339; 5,187,288; 5,248,782; 5,274,113; and 5,433,896), a xanthene (including any corresponding compounds disclosed in U.S. Pat. Nos. 6,162,931; 6,130,101; 6,229,055; 6,339, 392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Preferred fluorophores of the invention include xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the specific binding partner will determine the absorption and fluorescence emission properties of the reporter molecule and subsequent selection of the ASE. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also preferred chromophores of the present invention.

Fluorescent proteins may also find use as labels in the present invention. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorphore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556, and the sulforhodamine fluorophores disclosed in 5,798,276, or the sulfonated cyanine fluorophores disclosed in U.S. Ser. Nos. 09/968,401 and 09/969,853; or the sulfonated xanthene derivatives disclosed in U.S. Pat. No. 6,130,101, and those combinations disclosed in U.S. Pat. No. 4,542,104. Alternatively, the fluorophore functions as the energy donor and the fluorescent protein is the energy acceptor.

In one embodiment, the label is a fluorophore selected from the group consisting of fluorescein, coumarins, rhodamines, 5-TMRIA (tetramethylrhodamine-5-iodoacetamide), (9-(2 (or 4)-(N-(2-maleimdylethyl)-sulfonamidyl)-4(or 2)-sulfophenyl)-2,3,6,7,12,13,16,17-octahydro-(1H,5H,11H,15H-xantheno(2,3, 4-ij:5,6,7-i'j')diquinolizin-18-ium salt) (Texas Red®), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy™3), N,N'-dimethyl-N-(iodoacetyl)-N'-(7-nitrobenz-2-oxa-1,3-diazol-4-yl)ethylenediamine (IANBD amide), 6-acryloyl-2-dimethylaminonaphthalene (acrylodan), pyrene, 6-amino-2,3-dihydro-2-(2-((iodoacetyl)amino)ethyl)-1,3-dioxo-1H-benz(de)isoquinoline-5,8-disulfonic acid salt (lucifer yellow), 2-(5-(1-(6-(N-(2-maleimdylethylyamino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy™5), 4-(5-(4-dimethylaminophenyl)oxazol-2-yl)phenyl-N-(2-bromoacetamidoethyl)sulfonamide (Dapoxyl® (2-bromoacetamidoethyl)sulfonamide)), (N-(4,4-difluoro-1, 3,5,7-tetramethyl-4-bora-3a,4a-diaza-s-indacene-2-yl)iodoacetamide (BODIPY® 507/545 IA), N-(4,4-difluoro-5,7-diphenyl-4-bora-3a,4a-diaza-s-indacene-3-propionyl)-N'-iodoacetylethylenediamine (BODIPY 530/550 IA), 5-(((((2-iodoacetyl)amino)ethyl)amino)naphthalene-1-sulfonic acid (1,5-IAEDANS), and carboxy-X-rhodamine, 5/6-iodoacetamide (XRIA 5,6). Another example of a label is BODIPY-FL-hydrazide. Other luminescent labels include lanthanides such as europium (Eu3+) and terbium (Tb3+), as well as metal-ligand complexes of ruthenium [Ru(II)], rhenium [Re (I)], or osmium [Os(II)], typically in complexes with diimine ligands such as phenanthroline.

In another embodiment the reporter molecules are fluorgenic wherein they become fluorescent when associated with the analyte. Such reporter molecules include dyes that associate with nucleic acid (DNA and/or RNA), proteins (total and subsets such as post-translationaly modified proteins), pH, and metal ions. Reporter molecules for the detection of nucleic acid typically include unsymmetrical cyanine compounds, either monomers or dimmers, including, but not limited to compounds disclosed in U.S. Pat. Nos. 4,957,870; 4,883,867; 5,436,134; 5,658,751, 5,534,416; 5,863,753; 5,410,030; 5,582,977; 6,664,047; U.S. Ser. Nos. 10/911,423; 11/005,860; 11/005,861; 60/680,243 and WO 93106482; ethidium dimers (U.S. Pat. No. 5,314,805), acridine dimers and acridine-ethidium heterodimers (U.S. Pat. No. 6,428,667 and Rye, et al. Nucleic Acids Research (1990) 19(2), 327).

The following references describe DNA intercalating fluorescent dimers and their physical characteristics: Gaugain et al., Biochemistry (1978) 17:5071-5078; Gaugain et al., Biochemistry (1978) 17:5078-5088; Markovits et al., Anal. Biochemistry (1979) 94:259-269; Markovits et al. Biochemistry (1983) 22: 3231-3237; and Markovits et al., Nucl. Acids Res. (1985) 13:3773-3788. Commercially available dyes include PicoGreen, RiboGreen and OliGreen (Invitrogen).

In another embodiment the reporter molecules stain proteins, either directly or by forming a ternary complex comprising a metal ion. Such reporter molecules include, but are not limited to those disclosed in U.S. Pat. No. 5,616,502; U.S. Ser. Nos. 11/241,323; 11/199,641; 11/063,707; 10/966,536; 10/703,816; and 6,967,251. Commercially available dyes include NanoOrange, and Coomassie Fluor (Invitrogen).

In another embodiment the reporter molecules become fluorescent after associating with ions. Such reporter molecules include, but are not limited to those disclosed in U.S. Pat. Nos. 6,316,267; 6,162,931; 5,648,270; 6,013,802; 5,405,975; 5,516,864; 5,453,517; 6,962,992; U.S. Ser. Nos. 10/634,336; and 11/191,799. Commercially available dyes include fluo-3, fluo-4, Corona Red, Corona Green, Leadmuin Green, Fura Calcium Indicators.

Particular Aspects of the Invention:

One aspect of the present invention provides device for measuring the quantity of one or more predetermined analytes using a reporter molecule, wherein the device is an integrated unit which comprises a receptacle for holding a sample container having an analyte and the reporter molecule, a photodetector, one or more fixed and distinct analyte sensing elements (ASE) and a computer processing unit with machine executable instructions, wherein the ASE comprises:

a) an energy source for exciting the sample, wherein the energy source is configured to emit a predetermined peak wavelength of light;

b) an excitation filter, wherein the excitation filter is configured to isolate a predetermined range of wavelengths of light from the energy source;

c) an emission filter, wherein the emission filter is configured to isolate a predetermined range of wavelengths of light emitted from the excited sample; and wherein each of the ASE is configured to measure the quantity of the predetermined analyte and wherein the machine executable instructions are configured to select the proper ASE corresponding to the analyte to be measured.

In a preferred embodiment, the energy source is a light emitting diode (LED).

In another embodiment, the predetermined analyte is selected from the group consisting of DNA, RNA, protein, eukaryotic or prokaryotic cells, carbohydrates, lipids, viruses, pH and metals ions. In another embodiment, the machine executable instructions are further configured to determine the concentration of the specific analyte based upon an emitted light from the excited sample. In another embodiment, the device further comprises a user interface. In another embodiment, the user interface comprises a display and a non-numerical keypad.

In another embodiment, the sample container receptacle is configured to fit an optically clear 0.5 microcentrifuge tube. In another embodiment, the device further comprises an internal power source. In another embodiment, the device further comprises at least one communications port. More particularly, the communications port is selected from the group consisting of a universal serial bus (USB) port, an audio/video serial bus (IEEE 1394), an infrared (IR) port and a radio frequency (RF) port.

In another embodiment, the device comprises a first and second ASE. More particularly, the first ASE comprises a LED that emits light with a peak wavelength of about 470 nm, an excitation filter that filters out light with a wavelength of greater than about 490 nm and an emission filter that filters out light with a wavelength of less than about 520 nm and greater than about 580 nm. More particular still, the second ASE comprises a LED that emits light with a peak wavelength of about 640 nm, an excitation filter that filters out light with a wavelength of less than about 570 and greater than about 647 nm and an emission filter that filters out light with a wavelength of less than about 652 nm.

In another embodiment, the user interface is configured to allow a user to select the analyte for measurement.

In another embodiment, the machine executable instructions are capable of selecting the analyte for measurement without user input.

The device of claim 1, wherein dimensions of the device are about 30-300 mm on a minor axis, 100-500 mm on a major axis, and a variable thickness of about 10 to 100 mm; with the proviso that the dimension of the major axis is greater than the minor axis.

Another aspect of the invention provides a method of calculating the quantity of an analyte in an optically clear sample container, the method comprising
  a) generating a fluorescence standard curve comprising measuring the fluorescence intensity of a blank sample (g) and measuring the fluorescence intensity of at least one high-end standard (v), wherein the curve correlates fluorescence intensity to analyte quantity, and wherein the curve has a predetermined degree of sigmoidicity (n) and curvature (k);
  b) measuring the fluorescence intensity of the sample (y), wherein the sample comprises a fluorescent moiety capable of indicating the presence of the analyte in the sample; and
  c) correlating the fluorescence intensity in the sample (y) to the quantity of the analyte using the fluorescence standard curve.

In another embodiment, the curve is characterized by the equation:

$$y = r(x^n/(x^n+k)) + g; \quad (I)$$

wherein r is a correctional value determined by the formula:

$$r = (v-g)((s^n+k)/s^n) \quad (II)$$

wherein (s) is the quantity of analyte in the high-end standard.

Another embodiment provides a method for detecting the presence of a predetermined analyte in a sample wherein the sample is in an optically clear sample container, the method comprising:
  a) contacting the sample with a reporter molecule to form a contacted sample:
  b) detecting the presence of the predetermine analyte, wherein detecting comprises placing the optically clear container in a receptacle for holding the sample container of an integrated device for the measurement of a predetermined analyte, wherein the device further comprises:
  i) a photodetector, one or more fixed and distinct analyte sensing elements (ASE) and a computer processing unit with machine executable instructions, wherein the ASE comprises:
    an energy source for exciting the sample, wherein the energy source is configured to emit a predetermined peak wavelength of light;
    an excitation filter, wherein the excitation filter is configured to isolate a predetermined range of wavelengths of light from the energy source;
    an emission filter, wherein the emission filter is configured to isolate a predetermined range of wavelengths of light emitted from the excited sample; and
    wherein each of the ASE is configured to measure the quantity of the predetermined analyte and wherein the machine executable instructions are configured to select the proper ASE corresponding to the analyte to be measured.

Another aspect of the invention provides a method of calculating the ratio of two analytes in a sample container, the method comprising
  a) generating a fluorescence standard curve for the two analytes comprising: measuring the fluorescence intensity of a first blank analyte sample (g1) and a second analyte sample (g2) and measuring the fluorescence intensity of at least one high-end standard for the first analyte (v1) and at least one high-end standard for the second analyte (v2), wherein the curve correlates fluorescence intensity to each analyte quantity or relative quantity, and wherein the curves have a predetermined degree of sigmoidicity (n) and curvature (k);
  b) measuring the fluorescence intensity of the samples (y1 and y2), wherein the sample comprises a fluorescent moiety capable of indicating the presence of the analytes in the sample; and
  c) correlating the fluorescence intensity in the samples (y1 and y2) to the quantity of the analyte using the fluorescence standard curve.

Another embodiment of the invention provides, a method of detecting an enzyme or cleavage substrate in a sample, the method comprising:
  providing a device as described herein comprising a receptacle comprising a label bound to a cleavable linker, wherein the cleavable linker is cleaved by the enzyme or cleavage substrate;
  adding a sample suspected of containing the enzyme or cleavage substrate to the receptacle;
  monitoring a target section of the receptacle other than the site occupied by the label when bound to the cleavable linker; and
  detecting the presence of the label in the target section of the receptacle.

In a preferred embodiment thereof, the enzyme or cleavage substrate cleaves the cleavable linker, thereby releasing the label which diffuses to a section of the receptacle that is monitored for presence of the label. In another embodiment, the label is a fluorescent dye.

Preferred aspects of the invention include any one of the aspects of the invention, more particularly defined by the embodiments described herein.

In another embodiment the device is housed in an ellipse or oval shaped unit having dimensions of about 30-300 mm on the minor axis, 100-500 mm on the major axis, and a variable thickness of about 10 to 100 mm; with the proviso that the length of the major axis is greater than the minor axis. In a preferred embodiment, the unit has a decreasing thickness approaching the user, such that the screen is tilted toward the user. More particularly the unit is housed in a material with approximately 2-3 mm thickness. More particularly, the housing material is plastic.

In a particular embodiment, the device described has the design/structural features depicted in U.S. Design application Ser. No. 29/251,820, the contents of which are incorporated by reference as if set forth fully herein.

AIDS Diagnostic Test Device

Recent advances in CD4 diagnostic assays allow 2 simple reagents for use in identifying and counting two cell populations in whole blood, which is compatible with a simple fluorometer with 2 channels. The use of simple separations mechanism, such as a hand-crank centrifuge, simple cell filters or magnetic beads, separates the cells to be counted from the reagents. These 3 components comprise the AIDS Diagnostic Platform for Use in Remote Areas (ADPURA).

The key biochemical reagents for this application are the anti-CD4 antibody and the anti-CD45 antibody. These two antibodies are the basis for the PLG method (Glencross et al (2002) CD45 assisted panleucogating for accurate, cost effective dual platform CD4+ T cell enumeration, Cytometry Clinical Cytometry, Special Issue: CD4: 20 years and counting: 50 (2) 69-77) measures CD4+ cells using CD45-expressing cells (all white blood cells) for normalization. Using the two antibodies together (anti-CD4 antibody and anti-CD45 antibody) makes the CD4 count as simple as taking the ratio between CD4-expressing cells and CD45 expressing cells.

In one embodiment of the present invention, the following components are used together:
  a) A fluorometer having 2 detection channels, each comprised of an LED, an emission filter and a photodiode detector. The fluorometer has a user-interface and data analysis on a CPU (central processing unit) on a printed circuit board. The body is robust and can withstand environments with wind, sand and water present, different LEDs and emission filters, a streamlined user interface and fewer buttons. In addition, the fluorometer may work off of either a battery, handcrank or other power source not requiring a plug into an electric grid infrastructure. The fluorometer is designed for one purpose only, in which case the user-interface is simplified to express the result of the reading and one button only would be needed to activate the instrument to perform a reading. Alternatively, multiple diagnostic applications can be performed, with new applications capable of being loaded onto the instrument using a "thumb drive" with a USB connection.
  b) A reagent kit, which includes CD4 antibodies, labeled with a fluorescent dye, such as AlexaFluor 488 dye and CD45 antibodies, labeled with a fluorescent dye spectrally distinct from the CD4 label, such as Alexa Fluor 647 dye. The antibodies would ideally be stabilized for transport in hot or cold conditions, perhaps lyophilized, or perhaps an azide. Some alternate antibody-stabilization technology exists, which could be employed. The antibodies would be at the appropriate concentrations and in the appropriate containers to allow simple addition to the sample by person with little scientific training.
  c) One of three possible cell-separation platforms:
    a. CD45 antibody-labeled Dynal beads and DetachaBead technology to isolate the white blood cells from the whole cell population and then from the remaining beads using a simple magnet.
    b. A hand-crank centrifuge for 500 uL tubes that could be used to pellet the cells, combined with a simple plastic pipette to remove the supernatant and add washing solution. The centrifuge would be similar in principle to current hand-crank centrifuges on the market, but modified to use 500-uL plastic tubes, to be enclosed for operator safety as well as sample integrity, to be of a size similar to current tabletop "picofuges," and to be compatible with field conditions.
    c. A filter to separate the cells from the labeled CD4 and CD45 antibodies.
  d) Optional accessories to this platform would include inexpensive plastic pipettes and a water purification system, such as those found at stores that sell camping supplies.
  e) The invention further includes a kit comprising the above components, with the cell-labeling method, the cell-separations method and the fluorometer working seamlessly together.

The workflow for this application is as follows.
  a. First, the blood sample is taken from the patient and prepared for antibody staining using an accepted method.
  b. Second, the sample is mixed with the antibodies in the reagent kit. Fluorophore-labeled CD4 antibodies will bind to CD4+ cells and fluorophore-labeled CD45 antibodies will bind to CD45+ cells. If antibody-labeled beads are used for the separation method, these will bind to the cells as well during this step.
  c. Third, a separation method will be employed to remove the free labeled antibodies from the labeled cells.
    i. If this method uses the magnetic beads, a magnet will be used to remove the CD4+ and CD45+ cells from the sample. The supernatant will be discarded and the beads resuspended in a buffer. The beads will then be removed, for example, by using DetachaBead technology, applying the magnet to pull out the beads, leaving the labeled cells in the supernatant.
    ii. If the method uses a centrifuge, the sample will be spun in the centrifuge to pellet the labeled cells. The supernatant containing free labeled antibodies will be discarded and the cells resuspended in buffer.
    iii. If the method uses a filter, the sample will be applied to the filter, which will trap the labeled cells. The flow-through will be discarded and the labeled cells resuspended in buffer.
  d. Fourth, the sample will be read using the fluorometer. The labeled cells from step c will be transferred to a 500 uL clear PCR tube and read in the fluorometer. The fluorometer will be automated to take a reading in both channels, perform a calculation and express the value on an LCD or similar screen as a CD4+ count using standard nomenclature for this test.

In another embodiment the calibrators may be analytes at a known concentration. For example a blank containing zero analyte representing the low end of the assay and a tube containing a high concentration of analyte representing the high end of the assay when incubated with the appropriate analyte detecting dye.

In another embodiment the calibrators may be a liquid or solid standard that produces a fluorescent signal that is equal to corresponding analyte/dye mixtures.

In another embodiment the label may be fluorescent or light scattering nanocrystals [Yguerabide, J. and Yguerabide, EE, 2001 J. Cell Biochem Suppl.37: 71-81; U.S. Pat. Nos. 6,214,560; 6,586,193 and 6,714,299]. These fluorescent nanocrystals can be semiconductor nanocrystals or doped metal oxide nanocrystals. Nanocrystals typically are comprised of a core comprised of at least one of a Group II-VI semiconductor material (of which ZnS, and CdSe are illustrative examples), or a Group III-V semiconductor material (of which GaAs is an illustrative example), a Group IV semiconductor material, or a combination thereof. The core can be passivated with a semiconductor overlayering ("shell") uniformly deposited thereon. For example, a Group II-VI semiconductor core may be passivated with a Group II-VI semiconductor shell (e.g., a ZnS or CdSe core may be passivated with a shell comprised of YZ wherein Y is Cd or Zn, and Z is S, or Se). Nanocrystals can be soluble in an aqueous-based environment. An attractive feature of semiconductor nanocrystals is that the spectral range of emission can be changed by varying the size of the semiconductor core.

Figure 4:
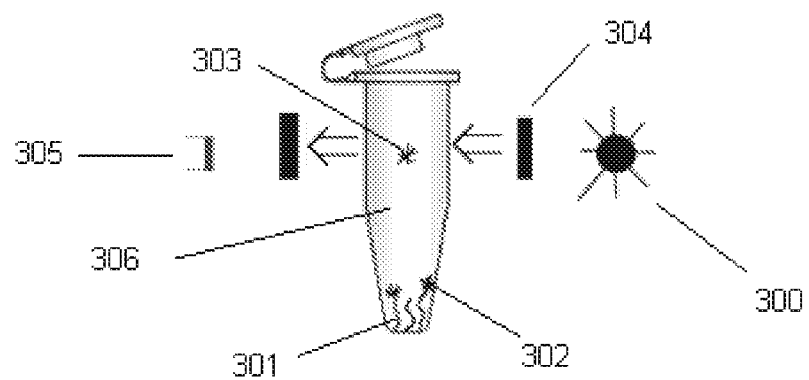
FIG. 4 depicts a device to measure the cleavage of a reporter from a zone outside of the optical path of the instrument to one within the optical path through diffusion or active mixing.

Embodiments using in situ cleavage:

In another embodiment the instrument may measure the cleavage of a reporter from a zone outside of the optical path of the instrument to one within the optical path through diffusion or active mixing. FIG. 4: Depicts a tube (306) inside the instrument. Reporter elements (302) bound to a cleavable substrate (301) are bound to the bottom of the tube. Once the substrate is cleaved then the reporter element is free (303) to travel inside the tube to within the optical path (300), of the instrument (304) where it is detected (305).

The Reporter element may be fluorescent or colorimetric.

The Cleavable substrate may be a nucleic acid, peptide, or other organic chemical.

The cleavable substrate may be cleaved by an enzyme or a chemical reaction.

The cleavable substrate may be attached to the tube or some other physical immobilizer such as magnetic or non-magnetic beads.

It is also possible that the rather than a cleavable substrate the reporter element may be displaced from a bound binder. Examples of such are fluorescent labeled desthiobiotin which could be displaced from Streptavidin by the higher affinity binding biotin.

Embodiments using multiple parameter device:
a. In another embodiment the machine executable instructions may be developed by the end-user "off-line" on a computer. Such that the name of the assay, appropriate ASEs, values and number of relevant calibrators, curve fitting algorithm, and format of displayed output are determined and set by the end-user and then "uploaded" to the instrument via a connecting cable.
b. Once "uploaded" to the instrument the new program would become a permanent selectable option on the instrument.

Dyes for cellular assays:

Dyes for Total Cell counting: SYTO 9, 11-18, 20-25, and 59-64, BC, TOTO-3, TO-PRO-3, DRAQ-5, DiI, DiO, WGA-546, FM1-43, Calcein AM Dyes for Dead Cell counting: SYTOX Green, SYTOX Red, SYBR Gold, SYBR Green, PicoGreen Preparation of a liquid standard:
a. Mix sample of high concentration calibration point that is liquid standard is intended to emulate. For example in the Quant-iT DNA High Sensitivity Assay the high standard is 100 ng lambda DNA plus PicoGreen dye (final concentration 0.7 uM) in a final volume of 200 uL TE.
b. Read relative fluorescent value on instrument (such as the Fluorometer described herein). For example in the Quant-iT DNA High Sensitivity Assay read using the 460 nm excitation source.
c. Stepwise add concentrated stable fluorescent compound to a diluting solution. For example in the Quant-iT DNA High Sensitivity Assay add concentrated fluorescein (10 mM in 0.1M Sodium Borate, pH9 buffer) to a solution of 0.1M Sodium Borate, pH 9 buffer until the fluorescent signal in the device equals that obtained in step b (approximate concentration 100 nM fluorescein).
d. For all experiments going forward substitute fluorescein solution for high standard. For example in the Quant-iT DNA High Sensitivity Assay substitute the 100 nM fluorescein calibrator for the calibrator containing 100 ng DNA plus PicoGreen.

In one embodiment of the present invention, the device described herein is used for water and soil testing. In a more particular embodiment thereof the device monitors for an alalyte or parameter selected from the group consisting of fecal coliform, pH, heavy metals, nitrates, arsenic, prions, Volatile Organic Compounds (VOC), chlorine, calcium, sodium, and glucose.

In another embodiment, the device described herein is used for infectious disease detection and monitoring. In a more particular embodiment thereof the device monitors for analyte or parameter selected from the group consisting of AIDS (CD4 assay), malaria, TB, SARS, BSE, Anthrax, Flu, Colds, Plague, and Prions.

In another embodiment, the device described herein is used for detection or identification of biomarkers. In a more particular embodiment thereof the biomarker is indicative of: cancer, mycoplasma, pregnancy, telomerase, antibodies, and genetic diseases.

In another embodiment, the device described herein is used for detection or identification of enzyme substrates. In a more particular embodiment thereof, the enzyme substrate is selected from the group consisting of: nucleases, phosphotases, glycoases, kinases, proteases and peroxidases.

In another embodiment, the device described herein is used for cell biology reagent validation and quality control (QC). In a more particular embodiment thereof the device monitors for an analyte or parameter selected from the group consisting of sodium, calcium, glucose, magnesium, potassium, zinc, thallium, pH, oxygen, nitric oxide, carbon dioxide, chloride and enzyme substrates (nucleases, phosphotases, glycoeases, kinases, proteases and peroxidases).

In another embodiment, the device described herein is used for bacterial determination. In a more particular embodiment thereof the device monitors for analytes associated with red tide or *E. Coli*.

In another embodiment, the device described herein is used in the field of cosmetics. In a more particular embodiment thereof, the device monitors for Reactive Oxygen Species (ROS), bacterial contamination, live/dead cells, melamine determination, cholesterol In another embodiment, the device monitors for GFP, chlorophyll, or biowarfare agents.

In another embodiment, the device described herein is used for automotive purposes. More particularly, leak detection, oil detection, air conditioning, coolant detection.

In another embodiment, the device described herein is used in forensics; more particularly sample determination, such as the detection/quantification of blood, urine or sperm.

In another embodiment, the device described herein is used for agricultural detection/quantitation. More particularly, for the detection/quantitation of enzyme substrates, such as, phytases, cellulases and others enzyme substrates described herein.

In another embodiment, the device described herein is used in end-point PCR. More particularly, the device monitors/detects stains including, SYBR Green, PicoGreen, SYBR Gold, among others. In another embodiment, the device detects/monitors for molecular beacons. In another embodiment the device detects/monitors for isothermal amplification.

The present invention relates to devices and methods for quantifying multiple analytes. The terms "quantify" or "measure the quantity" as used herein are interchangeable. The quantitative measurement can be any measurement designed to provide the end-user with information regarding the amount of the analyte in the sample. Thus the measurement may be an absolute measurement of the analyte, such as mass, or the measurement may be a relative measurement, such as concentration or parts per million, etc. Of course, the quantity of analyte may be equal to zero, indicating the absence of the analyte sought, or that the analyte is below the detectable level of the assay as measured by the instrument. The quantity may simply be the measured energy as detected by the photodetector, without any additional measurements or manipulations. Alternatively, the quantity may be expressed as a difference, percentage or ratio of the measured value of the analyte to a measured value of another compound including, but not limited to, a standard. The quantity may even be expressed as a difference or ratio of the analyte to itself, measured at a different point in time.

The quantity of analyte may be determined directly from the detected energy value, or the detected energy value may be used in an algorithm, with the algorithm designed to correlate the detected energy value to the quantity of analyte in the sample. To that end, the machine executable instructions may also be configured to determine the quantity of the analyte based upon the detected energy value.

In one particular embodiment, the machine executable instructions perform a method of calculating the quantity of an analyte in a sample by generating a fluorescence standard curve and correlating the fluorescence intensity of the sample to a quantity of analyte using this fluorescence standard curve. In a more particular embodiment, the fluorescence standard curve can be generated by measuring the fluorescence intensity of a "blank" sample, i.e., a sample known to be without the analyte, (g) and measuring the fluorescence intensity of only one standard containing a known amount of the analyte (v). Of course, the fluorescence standard curve could be generated using more than one standard containing a known amount of the analyte. Once the fluorescence value of the blank and standard have been measured, the machine executable instructions can then generate the fluorescence standard curve. The fluorescence standard curve may have a predetermined degree of sigmoidicity (n) and curvature (k), prior to the measuring the blank and standard(s), and the machine executable instructions may possess these (k) and (n) values as part of the algorithm for generating the fluorescence standard curve. Once the machine executable instructions generate the fluorescence standard curve, the fluorescence intensity of a sample (y) can be measured and the (y) value can be correlated to an analyte quantity using the fluorescence standard curve.

In a specific embodiment, the fluorescence standard curve can be characterized by the following equation:

$$y = r(x^n/(x^n+k)) + g; \quad (I)$$

where (r) is a correctional value determined by the formula:

$$r = (v-g)((s^n+k)/s^n) \quad (II)$$

and where (s) is the quantity of analyte in the high-end standard.

In an even more specific embodiment, the value of (n) in equations I and II approach or are approximately equal to 1 (one). Values of n include but are not limited to, $0 \le n \le 10$, $0 \le n \le 5$, $0.5 \le n \le 3$, $0.75 \le n \le 1.5$, $0.8 \le n \le 1.2$, $0.9 \le n \le 1.1$ and $0.95 \le n \le 1.05$. In addition, the curve may approach linearity.

As k approaches infinity, the curve approaches linearity. It is readily understood what is meant when a curve "approaches linearity."

In another specific embodiment, three standards are used, where one standard is a blank, another standard is a mid-range standard and the third standard is the high-end standard. In this particular embodiment, (n) is predetermined, but (k) may be variable and thus should be determined. In this embodiment, k is solved for using equation IV below.

$$k = [s^n t^n (d-1)]/[s^n - (t^n d)] \quad (IV)$$

The value d is a correctional value that is equal to the ratio of the fluorescence value of the two non-blank background-corrected non-blank standards that is solved for using equation V below.

$$d = (v-g)/(w-g) \quad (V)$$

In equation V, (w) is the fluorescence intensity of the mid-range standard used in this assay, value (v) is the fluorescence intensity of the high-end standard and (g) is the fluorescence intensity of the blank. In equation IV, the (t) is the quantity of analyte in the mid-range standard.

Another embodiment provides a method of calculating the ratio of two analytes in a sample container, said method comprising
 a) generating a fluorescence standard curve for the two analytes comprising: measuring the fluorescence intensity of a first blank analyte sample (g1) and a second analyte analyte sample (g2) and measuring the fluorescence intensity of at least one high-end standard for the first analyte (v1) and at least one high-end standard for the second analyte (v2), wherein said curve correlates fluorescence intensity to each analyte quantity or relative quantity, and wherein said curves have a predetermined degree of sigmoidicity (n) and curvature (k);
 b) measuring the fluorescence intensity of said samples (y1 and y2), wherein said sample comprises a fluorescent moiety capable of indicating the presence of said analytes in said sample; and
 c) correlating said fluorescence intensity in said samples (y1 and y2) to the quantity of said analyte using said fluorescence standard curve.

Thus the present invention relates to a device for quantifying an analyte, with the device comprising machine executable instructions that implement the methods of quantifying an analyte utilizing a fluorescence standard curve equation I, above. This device may, of course, further comprise each of the components listed herein, such as, but not limited to, a receptacle for holding a sample container, photodetector, and one or more ASEs.

The computer processing unit may also comprise sufficient memory and instructions or operations for associating a sample identity tag with a particular sample. In this embodiment, the device may comprise a means for identifying an identity tag associated with a sample container. In one particular embodiment, the sample identity tag is machine readable. Examples of identity tags include, but are not limited to, barcodes, data matrix barcodes, radio frequency identity tags, optical tags and the like. The means for identifying the identity tag should, of course, be suited to the type of identity tag employed. In turn, the machine executable instructions may then be able to match the determined quantity value of the analyte with a particular sample, based on the sample identity tag.

The devices of the present invention may also comprise a user interface. Various user interfaces can be provided to facilitate user control and to enhance operability of the devices. Input interfaces include, but are not limited to, data entry devices such as a keyboard, keypad, touch-screen display, mouse, voice recognition input, or other data entry device. In one specific embodiment, the user interface comprises a non-numerical keypad. Output interfaces include, but are not limited to, a display screen, monitor, a printer, a speaker or other output device. In another specific embodiment, the user interface comprises a display screen. In yet another specific embodiment, the user interface comprises both a non-numerical keypad and a display screen. In a more specific embodiment, the user interface is configured to allow the end-user to select the analyte being quantified. Once the analyte is selected by the end-user, the machine executable instructions can then determine which ASE to employ, if necessary, to quantify the analyte.

The devices of the present invention may optionally comprise an internal power source, used to power the various components of the device. In one embodiment, the power source is rechargeable. In another embodiment, the internal power source is not rechargeable.

In another embodiment, the devices of the present invention may comprise one or more communications ports. The communications port(s) is (are) capable of connecting to another device such as, but not limited to, a computer, a disk drive, a flash memory drive, a monitor, a printer, another similar device for quantifying analytes. For example, the functions of the device can be updated or altered, and the device can be calibrated or recalibrated with new machine executable instructions from a computer, CD or DVD via the communications port. The devices are not limited by the types of communications ports. Examples of communications ports include bur are not limited to universal serial bus (USB), an audio/video serial bus (IEEE 1394) ("firewire"), and infrared port and a radio frequency port. Radio ports include Bluetooth® ports, Wi-Fi ports and the like.

In a particular embodiment of any of the aforementioned embodiments, the analyte is a eukaryotic or prokaryotic cell.

In another embodiment, the device or method described herein is used for quantification of DNA at low levels in liquid samples. In another embodiment the device or method described herein is used for quantification of DNA at broad ranges in a liquid sample. In another embodiment, the device or method is used for quantification of RNA in liquid samples. In another embodiment, the device or method is used for quantification of protein in liquid samples. In another embodiment, the device or method is used for quantification of live:dead cells in liquid samples. In another embodiment, the device or method is used for quantification of GFP expression levels in liquid samples. In another embodiment, the device or method is used for detection and quantification of *Mycoplasma* contamination of cell cultures and cell culture reagents. Further description of these embodiments are described in the Examples that follow.

EXAMPLES

Example 1

Analyzing RNA Concentrations $$y = r(x^n/(x^n+k)) + g; \quad \text{Using Equation I:}$$

where (r) is a correctional value determined by the formula:

$$r = (v-g)((s^n+k)/s^n) \tag{II}$$

the concentration of RNA in a sample is determined. The value (y) is the fluorescence intensity of the sample with an unknown concentration of analyte. The high-end standard, which is the value of (s), has a concentration of 500 ng/ml. The sigmoidicity (n) is set to a value of 1.10 and the curvature (k) is set to 2350. The fluorescence intensity of the blank (g) is 22.16 relative fluorescence units (RFU) and the fluorescence intensity of the high-end standard (v) is 543.97 RFU. These values are used in equation II to solve for r, which is 1839.20

Solving equation I for x, which is, in this example, the concentration of RNA in the sample, results in Equation III $$x = |(k(y-g))/(r-(y-g))|^{1/n} \tag{III}$$

Using a fluorometer of the present invention, the fluorescence intensity of a sample containing 400 ng/ml of RNA is measured as 459.40 RFU. Plugging this value into equation III, the fluorometer obtains a concentration value of RNA in the sample of 402.34 ng/ml.

Example 2

Analyzing DNA Concentrations at Low Levels

Using equations I, II and II from above, the concentration of low levels of DNA can also be assessed. In this example, the (n) is set to 1.00 and (k) is set to 9999999. The blank has a fluorescence value (g) of 7.61 RFU and the high-end standard has a fluorescence value (v) of 3020.30 RFU. The high-end standard (s) has a concentration of 500 ng/ml. Using these values in Equation II, the correctional value (r) is determined to be 60256806.66.

The sample contains 400 ng/ml of DNA and has a fluorescence value (y) of 2401.60. The concentration of DNA, using Equation III is determined to be 397.31 ng/ml.

Example 3

Analyzing DNA Over a Broad Range of Concentrations

Using equations I, II and II from above, the concentration of DNA can also be assessed. In this example, the (n) is set to 1.00 and (k) is set to 22.5. The blank has a fluorescence value (g) of 25.36 RFU and the high-end standard has a fluorescence value (v) of 2213.20 RFU. The high-end standard (s) has a concentration of 5 μg/ml. Using these values in Equation II, the correctional value (r) is determined to be 12033.12.

The sample contains 4.0 μg/ml of DNA and has a fluorescence value (y) of 1841.10. The concentration of DNA, using Equation III is determined to be 4.0 μg/ml.

Example 4

Analyzing Protein Concentrations

Using equations I, II and III from above, the concentration of protein can also be assessed. When assessing protein concentration, it may be desirable to use three standards rather than two standards as above.

If three standards are used, then k may be variable, and if k is variable, the algorithm will first solve for k using the three standards. Once k is solved for, the algorithm uses this value in equations I, II and III above. To solve for k when k is variable, using three standards, the follow equation is employed:

$$k = [s^n t^n (d-1)]/[s^n - (t^n * d)] \tag{IV}$$

where d is a correctional value that is equal to the ratio of the fluorescence value of the two non-blank background-corrected standards that is determined by equation V.

$$d=(v-g)/(w-g) \quad (V)$$

In equation V, w is the fluorescence value of the mid-range standard used in this assay. Once the correctional value d is determined, this value is plugged into equation IV to solve for (k). The value (s) is the concentration of the high-end standard, as in equation II, and (t) is the concentration of the mid-range standard, and (n) is predetermined. Once (k) is solved for, using equations IV and V, the fluorescence value of the unknown is measured (y) and the concentration of the unknown (x) is determined using equation III, as above.

In this example, the (n) is set to 2.15. The blank has a fluorescence value (g) of 42 RFU and the high-end standard has a fluorescence value (v) of 3230 RFU. The high-end standard (s) has a concentration of 5.000 µg/200 µl. The mid-range standard has a fluorescence value (w) of 1286 and a concentration (t) of 2.000 µg/200 µl. Using these values in Equations IV and V, (k) equals 10.79. Using k=10.79 and n=2.15 in equation II, the correctional value (r) (based on the high-end standard) equals 4371.28. Finally, the fluorescence value of a sample (y) containing 3.000 g/200 µl of protein is measured as 2334. The fluorometer, employing the algorithms described herein determines that the concentration of the sample is 3.2 µg/200 µl.

In the following Examples "Quant-it" assay firmware selections are connected to analyte sensing elements with predetermined algorithms, standards, light sources, filters, etc., as described above for the various types of analytes. These coordinated analyte sensing elements make the device very easy for the technician to operate.

Example 5

Quantification of DNA at Low Levels in Liquid Samples

PicoGreen dye, is diluted in a specific buffer to make a Working Dye Solution of 0.7 µM. Between 180 and 199 uL of the Working Dye Solution is added to a 500 uL clear plastic PCR tube, described herein. Two of the tubes are used for standards to calibrate the instrument for the assay. 10 uL of a solution of TE (10 mM Tris, 1 mM EDTA) is added as the "zero" to one tube. 10 uL of a 10 ng/uL solution of lambda DNA in TE is added to the second tube and is the high standard. To the remaining tubes, between 1 and 20 uL of an unknown sample is added, for a final concentration of 200 uL in each tube. Each of the tubes is mixed using a vortexer or by inverting the tube and then incubated at room temperature for 2 minutes. To determine the amount of DNA in the assay tube, the user chooses the "Quant-iT DNA HS" assay using the firmware built into the fluorometer, and then follows prompts to allow the fluorometer to read Standard 1 (the zero standard described above), Standard 2 (the high standard described above) and then any number of samples. Using the two standards, the instrument determines the concentration of DNA in the sample tubes using the equations described in Example 2. The concentration of DNA in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of DNA in the original sample tube is then displayed on the screen of the fluorometer. All of these data can be simultaneously transferred to a computer using the compatible ports and data logging software, described herein.

Example 6

Quantification of DNA at Broad Ranges in Liquid Samples

HiQuant dye, is diluted in a specific buffer to make a Working Dye Solution of 2 µM. Between 180 and 199 uL of this Working Dye Solution is added to a 500 uL clear plastic PCR tube, described herein. Two of the tubes are used for standards to calibrate the instrument for the assay. 10 uL of a solution of TE (10 mM Tris, 1 mM EDTA) is added as the "zero" to one tube. 10 uL of a 100 ng/uL solution of lambda DNA in TE is added to the second tube to serve as the high standard. To the remaining tubes, between 1 and 20 uL of an unknown sample is added, for a final concentration of 200 uL in each tube. Each of the tubes is mixed using a vortexer or by inverting the tube and then incubated at room temperature for 2 minutes. To determine the amount of DNA in the assay tube, the user chooses the "Quant-iT DNA BR" assay using the firmware built into the fluorometer, and then follows prompts to allow the fluorometer to read Standard 1 (the zero standard described above), Standard 2 (the high standard described above) and then any number of samples. Using the two standards, the instrument determines the concentration of DNA in the sample tubes using the equations described in Example 3. The concentration of DNA in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of DNA in the original sample tube is then displayed on the screen of the fluorometer. All of these data can be simultaneously transferred to a computer using the compatible ports and data logging software, described herein.

Example 7

Quantification of RNA in Liquid Samples

RiboRed dye, is diluted in a specific buffer to make a Working Dye Solution of 0.04 µM. Between 180 and 199 uL of this Working Dye Solution is added to a 500 uL clear plastic PCR tube, described herein. Two of the tubes are used for standards to calibrate the instrument for the assay. 10 uL of a solution of TE (10 mM Tris, 1 mM EDTA) is added as the "zero" to one tube. 10 uL of a 10 ng/uL solution of ribosomal RNA in TE is added to the second tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 2 minutes. To determine the amount of RNA in the assay tube, the user chooses the "Quant-iT RNA" assay using the firmware built into the fluorometer, and then follows prompts to allow the fluorometer to read Standard 1 (the zero standard described above), Standard 2 (the high standard described above) and then any number of samples. Using the two standards, the instrument determines the concentration of RNA in the sample tubes using the equations described in Example 2. The concentration of RNA in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of RNA in the original sample tube is then displayed on the screen of the fluorometer. All of these data can be simultaneously transferred to a computer using the compatible ports and data logging software, described herein.

Example 8

Quantification of Protein in Liquid Samples

NanoOrange dye, is diluted in a specific buffer to make a Working Dye Solution of 4 µM. Between 180 and 199 uL of this Working Dye Solution is added to a 500 uL clear plastic PCR tube, described herein. Three of the tubes are used for standards to calibrate the instrument for the assay. 10 uL of a solution of TE (10 mM Tris, 1 mM EDTA) is added as the "zero" to one tube. 10 uL of a 200 ng/uL solution BSA in TE is added to the second tube and will be the middle standard. 10 uL of a 400 ng/uL solution BSA in TE is added to the third tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 15 minutes. To determine the amount of protein in the assay tube, the user chooses the "Quant-iT Protein" assay using the firmware built into the fluorometer, and then follows prompts to allow the fluorometer to read Standard 1 (the zero standard described above), Standard 2 (the middle standard described above), Standard 3 (the high standard described above) and then any number of samples. Using the three standards, the instrument determines the concentration of protein in the sample tubes using the equations described in Example 4. The concentration of protein in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of protein in the original sample tube is then displayed on the screen of the fluorometer. All of these data can be simultaneously transferred to a computer using the compatible ports and data logging software, described herein.

Example 9

Quantification of Cells (Eukaryotic or Prokaryotic) in Liquid Samples

SYTO 9 dye, is diluted in a specific buffer to make a Working Dye Solution of 0.02 mM. Between 180 and 199 uL of this Working Dye Solution is added to a 500 uL clear plastic PCR tube, described herein. Two of the tubes are used for standards to calibrate the instrument for the assay. 200 uL of a solution of water is added as the "zero" to one tube. 200 uL of a 100 nM fluorescein solution in 0.1M Sodium Borate, pH 9 buffer is added to the second tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 5 minutes. To determine the amount of cells in the assay tube, the user chooses the "Quant-iT Cell Count" assay using the firmware built into the fluorometer, and then follows prompts to allow the fluorometer to read Standard 1 (the zero standard described above), Standard 2 (the high standard described above) and then any number of samples. Using the two standards, the instrument determines the concentration of protein in the sample tubes using the equations described herein (see equations I-V). The concentration of cells in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of cells in the original sample tube is then displayed on the screen of the fluorometer. All of these data can be simultaneously transferred to a computer using the compatible ports and data logging software, described herein.

Example 10

Quantification of Live:Dead Ratios of Cells (Eukaryotic or Prokaryotic) in Liquid Samples SYTO 9 dye and SYTOX Red dye, is diluted in a specific buffer to make a Working Dye Solution of 0.02 mM of each dye. Between 180 and 199 uL of this Working Dye Solution is added to a 500 uL clear plastic PCR tube, described herein. Two of the tubes are used for standards to calibrate the instrument for the assay. 200 uL of a solution of water is added as the "zero" to one tube. 200 uL of a 100 nM fluorescein dye and 100 nM Alexa Fluor 647 dye solution in 0.1M Sodium Borate, pH 9 buffer is added to the second tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 5 minutes. To determine the amount of live and dead cells in the assay tube, the user chooses the "Quant-iT Live/Dead" assay using the firmware built into the fluorometer, and then follows prompts to allow the fluorometer to read Standard 1 (the zero standard described above), Standard 2 (the high standard described above) and then any number of samples using both a "blue" channel (Ex/Em: 460 nm/520 nm) and a deep red channel (Ex/Em: 630 nm/650 nm) as described in [0031]. Using the two standards, the instrument determines the relative concentration of total cells and dead cells in the sample tubes using the equations described herein. The ratio of the two is displayed on the screen of the fluorometer. All of these data can be simultaneously transferred to a computer using the compatible ports and data logging software, described herein.

Example 11

Quantification of GFP Expression Levels in Cells in a Liquid Samples

SYTO 61 dye, is diluted in a specific buffer to make a Working Dye Solution of 0.02 mM. Between 180 and 199 uL of this Working Dye Solution is added to a 500 uL clear plastic PCR tube, described in [0016]. Two of the tubes are used for standards to calibrate the instrument for the assay. 200 uL of a solution of water is added as the "zero" to one tube. 200 uL of a 100 nM fluorescein dye and 100 nM Alexa Fluor 647 dye solution in 0.1M Sodium Borate, pH 9 buffer is added to the second tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 5 minutes. To determine the amount of cells in the assay tube, the user chooses the "Quant-iT GFP" assay using the firmware built into the fluorometer, and then follows prompts to allow the fluorometer to read Standard 1 (the zero standard described above), Standard 2 (the high standard described above) and then any number of samples using both a "blue" channel (Ex/Em: 460 nm/520 nm) and a deep red channel (Ex/Em: 630 nm/650 nm) as described in [0031]. Using the two standards and the signal from the SYTO 61, the instrument determines the concentration of cells in the sample tubes using the equations described in [0066]. Using the two standards and the signal from the "blue" channel, the instrument determines the concentration of GFP in the sample tube using the equations described in [0066]. The ratio of GFP to cell concentration in the solution in the assay tube is displayed on the screen of the fluorometer. All of these data can be simultaneously transferred to a computer using the compatible ports and data logging software, described herein.

Example 12

Detection and Quantification of *Mycoplasma* Contamination of Cell Cultures, and Cell Culture Reagents GFP is covalently attached to one end of a peptide that is bound to the bottom of a 500 uL clear plastic tube. Between 180 and 199 uL of this Working Solution is added to a 500 uL clear plastic PCR tube, described herein. Two of the tubes are used for standards to calibrate the instrument for the assay. 200 uL of a solution of water is added as the "zero" to one tube. 200 uL of a 100 nM fluorescein solution in 0.1M Sodium Borate, pH 9 buffer is added to the second tube and will be the high standard. To the remaining tubes, between 1 and 20 uL of an unknown sample is added, for a final concentration of 200 uL in each tube. Each of the tubes is mixed using a vortexer or by inverting the tube and then incubated at room temperature for 5 minutes. To determine the presence of *Mycoplasma* contamination, the user chooses the "Quant-iT *Mycoplasma*" assay using the firmware built into the fluorometer, and then follows prompts to allow the fluorometer to read Standard 1 (the zero standard described above), Standard 2 (the high standard described above) and then any number of samples. Using the two standards, the instrument determines the concentration of *Mycoplasma* in the sample tubes using the equations described herein. The concentration of *Mycoplasma* in the solution in the assay tube is displayed on the screen of the fluorometer. An option is included in the firmware to perform a dilution calculation by asking the user to choose from 1, 2, 3, 4, 5, 10, 15 or 20 uL of the sample added to the sample tube. The concentration of *Mycoplasma* in the original sample tube is then displayed on the screen of the fluorometer. All of these data can be simultaneously transferred to a computer using the compatible ports and data logging software, described herein.

Example 13

Prokaryotic Live:Dead Determination 2 mL of *S. aureus* are collected into microcentrifuge tube and pellet. One tube is treated with 70% IPA (Isopropyl Alcohol)-30 min RT to kill cells and then Washed/Spinned 2×. Pellets are resuspended and transferred into 10 mL 0.85% NaCl. Test solutions are prepared with ratios depicted in Table 1, and appropriate stain is added: 0.3 uL of 3.35 mM SYTO 9 and/or 1 uL of 1 mM SYTOX Red. The solutions are incubated for 15 min at RT, 200 uL are transferred to a PCR tube and analyzed.

TABLE 1

| | Live:Dead Ratio | | | |
|---|---|---|---|---|
| | 1 | 2 | 3 | 4 |
| A | 100:0 | 100:0 | 100:0 | 100:0 |
| B | 50:50 | 50:50 | 50:50 | 50:50 |
| C | 0:100 | 0:100 | 0:100 | 0:100 |
| Stain→ | No Stain | SYTO 9 | SYTOX Red | SYTO 9 & SYTOX Red |

Figure 5A:
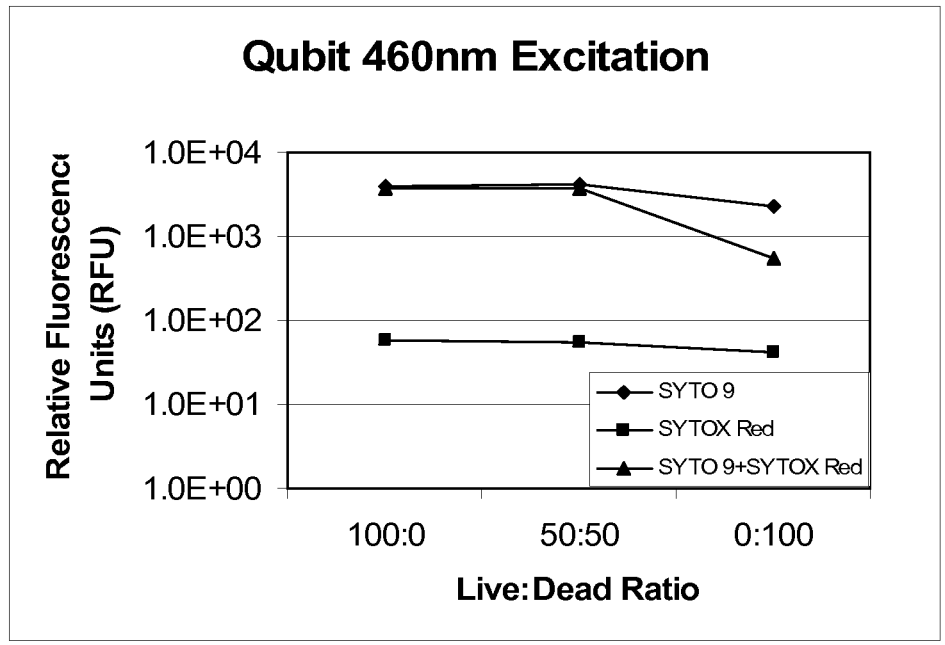
FIG. 5A depicts blue excitation signal as the ratio of Live:Dead cells decreases.

Results:

Blue Excitation—SYTO 9 shows little change in signal as the ratio of Live:Dead cells decreases. SYTOX Red is not optimally excited by 460 nm excitation (see FIG. 5A).

Figure 5B:
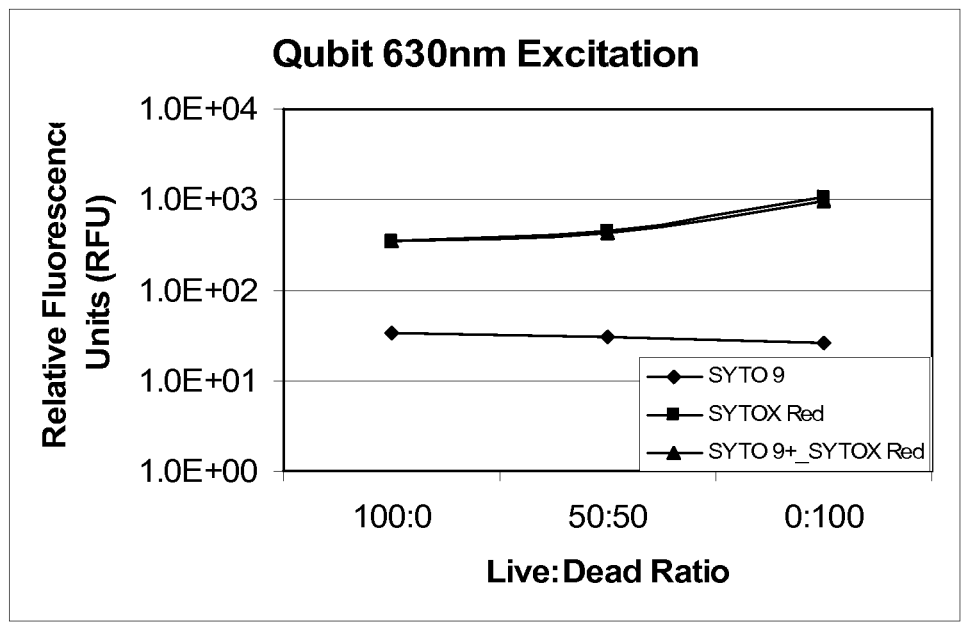
FIG. 5B depicts red excitation signal increasing as the ratio of Live:Dead cells decrease.

Red Excitation—SYTOX Red signal increases as the ratio of Live:Dead cells decrease. SYTO 9 is not optimally excited by 460 nm excitation (see FIG. 5B).

Figure 5C:
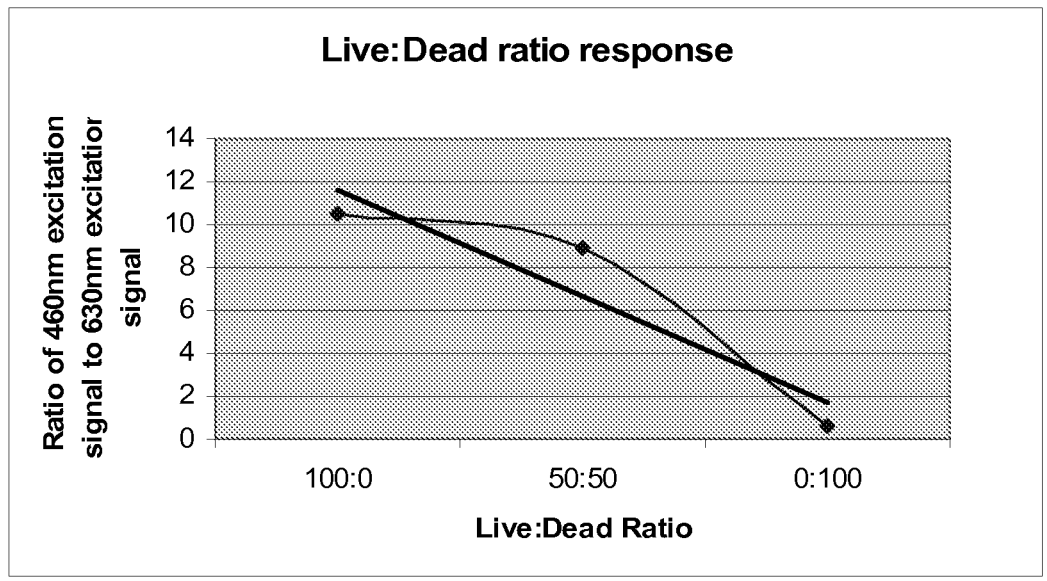
FIG. 5C depicts ratio determination of Live:Dead cells.

Ratio Determination—As the ratio of Live:Dead cells decreases the SYTO 9 signal decreases slightly, while the SYTOX Red signal increases significantly as it stains the dead cells. The ratio between the signal from the 460 nm source (exciting only SYTO 9) and the signal from the 630 nm source (exciting only SYTOX Red) decreases proportionally to the live:dead ratio of the cells (see FIG. 5C).

Example 14

Eukaryotic Cell Counting

Eukaryotic Cell Line (Jurkat, MRCS, U2OS, 3T3, BPAE, COS, HeLa, CHO-K1) are collected and cell concentration are counted and set equal ($1 \times 10^6$ cells/mL) using the Coulter Counter. 1 mL of cells are mixed with SYTO 9 (final concentration 1 uM) for 15 minutes at RT. 200uL of the solution is transferred to a PCR tube and read using 460 nm excitation.

Figure 6:
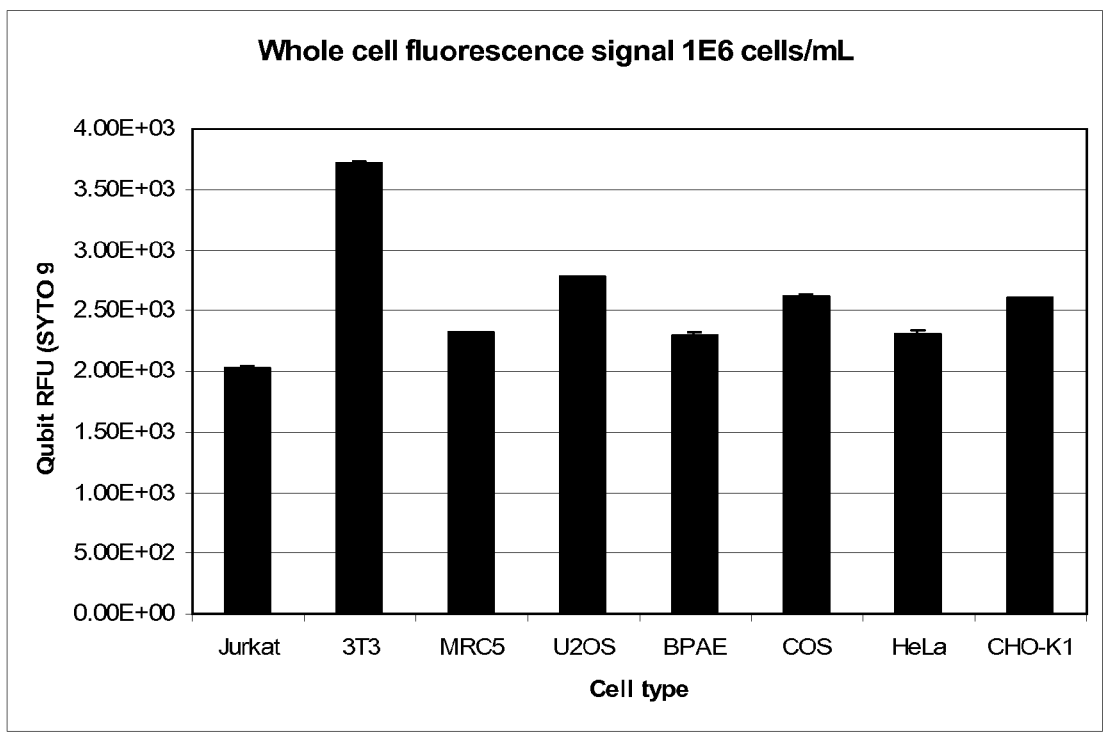
FIG. 6 depicts Eukaryotic cell counting on the device described herein, wherein a fluorescent response is displayed for all eukaryotic cell lines tested significantly above background.

Results: 460 nm excitation—SYTO 9 shows a fluorescent response for all eukaryotic cell lines tested significantly above background (see FIG. 6).

Each of the aforementioned references are hereby incorporated by reference as is set forth fully herein.

What is claimed is:

1. A device for measuring the quantity of one or more predetermined analytes, comprising:
    an integrated unit including a receptacle for holding a sample container having an analyte, a photodetector, two or more distinct and operably linked analyte sensing elements (ASE) and a computer processing unit with machine executable instructions, wherein each ASE comprises:
    a distinct energy source for exciting the sample, wherein the energy source is configured to emit a predetermined peak wavelength of light; and
    wherein each ASE is configured to facilitate the measurement of the quantity of the predetermined analyte and wherein the machine executable instructions are configured to select the proper ASE corresponding to the analyte to be measured.

2. The device of claim 1, wherein each ASE further includes an emission filter configured to isolate a predetermined range of wavelengths of light emitted from the excited sample.

3. The device of claim 1, wherein the predetermined analyte is selected from the group consisting of DNA, RNA, protein, eukaryotic or prokaryotic cells, carbohydrates, lipids, viruses, pH, dyes and metals ions.

4. The device of claim 1, wherein the machine executable instructions are further configured to determine the concentration of the specific analyte based upon an emitted light from the excited sample.

5. The device of claim 1, wherein the device further comprises a user interface.

6. The device of claim 5, wherein the user interface comprises a display and a non-numerical keypad.

7. The device of claim 1, wherein the sample container receptacle is configured to fit an optically clear 0.5 mL microcentrifuge tube.

8. The device of claim 1, wherein the device further comprises an internal power source.

9. The device of claim 1, further comprising at least one communications port.

10. The device of claim 9, wherein the communications port is selected from the group consisting of a universal serial bus (USB) port, an audio/video serial bus (IEEE 1394), an infrared (IR) port and a radio frequency (RF) port.

11. The device of claim 1, wherein the device comprises a first and second ASE.

12. The device of claim 11, wherein the first ASE comprises a LED that emits light with a peak wavelength of about 470 nm, an excitation filter that filters out light with a wavelength of greater than about 490 nm and an emission filter that filters out light with a wavelength of less than about 520 nm and greater than about 580 nm.

13. The device of claim 11, wherein the second ASE comprises a LED that emits light with a peak wavelength of about 640 nm, an excitation filter that filters out light with a wavelength of less than about 570 and greater than about 647 nm and an emission filter that filters out light with a wavelength of less than about 652 nm.

14. The device of claim 5, wherein the user interface is configured to allow a user to select the analyte for measurement.

15. The device of claim 1, wherein the machine executable instructions are capable of selecting the analyte for measurement without user input.

16. The device of claim 1, wherein dimensions of the device are about 30-300 mm on a minor axis, 100-500 mm on a major axis, and a variable thickness of about 10 to 100 mm; with the proviso that the dimension of the major axis is greater than the minor axis.

* * * * *